United States Patent [19]
Obremski et al.

[11] Patent Number: 5,498,875
[45] Date of Patent: Mar. 12, 1996

[54] SIGNAL PROCESSING FOR CHEMICAL ANALYSIS OF SAMPLES

[75] Inventors: Robert J. Obremski, Yorba Linda; John W. Silzel, Orange, both of Calif.

[73] Assignee: Beckman Instruments, Inc., Fullerton, Calif.

[21] Appl. No.: 292,798

[22] Filed: Aug. 17, 1994

[51] Int. Cl.$^6$ ............................ G01N 21/64; G01N 21/65
[52] U.S. Cl. .................................. 250/458.1; 250/459.1; 356/73; 356/301; 356/317; 356/318
[58] Field of Search ............................ 250/458.1, 459.1; 356/301, 73, 317, 318

[56] References Cited

U.S. PATENT DOCUMENTS

| | | | |
|---|---|---|---|
| 3,788,742 | 1/1974 | Garbuny . | |
| 3,807,862 | 4/1974 | Hatzenbuhler . | |
| 4,011,013 | 3/1977 | Barrett . | |
| 4,284,354 | 8/1981 | Liao | 250/301 |
| 4,505,586 | 3/1985 | Tochigi et al. | 356/301 |
| 4,619,528 | 10/1986 | Genack et al. | 356/301 |
| 4,900,933 | 2/1990 | Nestor et al. | 250/458.1 |
| 4,927,265 | 5/1990 | Brownlee | 356/73 |
| 4,986,656 | 1/1991 | Sweeney et al. | 356/73 |
| 4,988,859 | 1/1991 | Tsuchiya et al. . | |
| 5,026,159 | 6/1991 | Allen et al. | 250/458.1 |
| 5,049,738 | 9/1991 | Gergely et al. | 250/301 |
| 5,185,521 | 2/1993 | Kvasnik et al. | 356/301 |
| 5,190,857 | 3/1993 | Allen et al. | 250/459.1 |
| 5,202,230 | 4/1993 | Kamentsky . | |
| 5,267,019 | 11/1993 | Whittaker et al. | 356/437 |

*Primary Examiner*—Carolyn E. Fields
*Attorney, Agent, or Firm*—William H. May; Gary T. Hampson; Sheldon & Mak

[57] ABSTRACT

A method and apparatus determines the analyte content of a sample by generating first and second input signals and directing the input signals to the sample. The input signals differ in wavelength by at least 3 nanometers. Due to the interaction between the input signals and the sample, first and second output signals are generated. Each output signal comprises a resonant signal whose peak wavelength is substantially independent of the wavelength of the respective input signal, and a non-resonant output signal whose peak wavelength is dependent upon the wavelength of respective input signal. A detector is used to detect the two output signals, and by distinguishing the resonant output signals from the non-resonant output signals, data about the analyte content of the sample is determined. Principal components regression analysis or multivariate quantitative analysis can be applied to the output signals, for the purpose of distinguishing between the resonant and non-resonant signals. The method and apparatus can also distinguish resonant output signals from each other, and non-resonant output signals from each other.

49 Claims, 12 Drawing Sheets

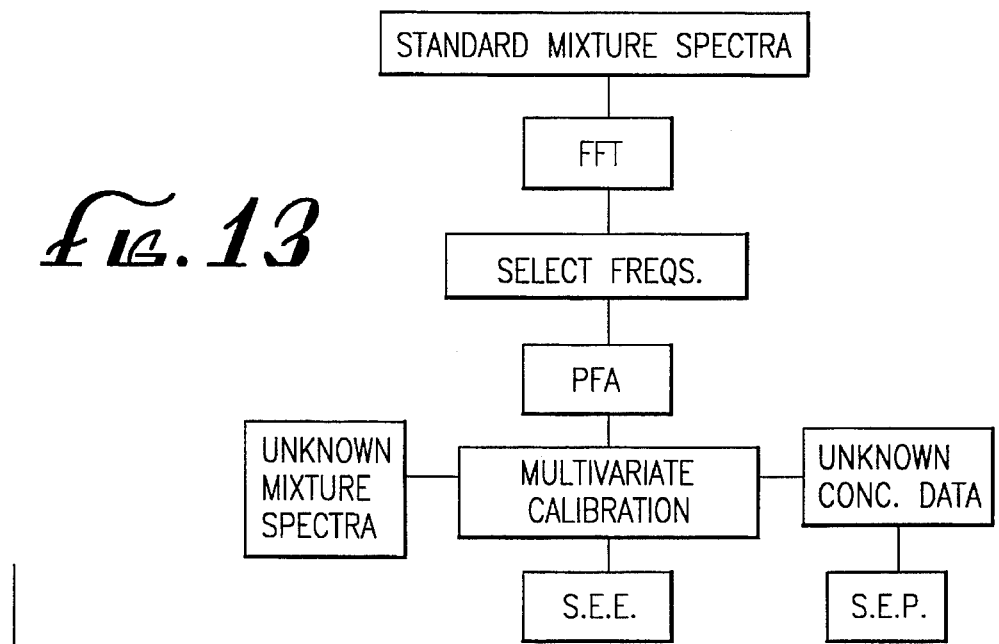
FIG. 13
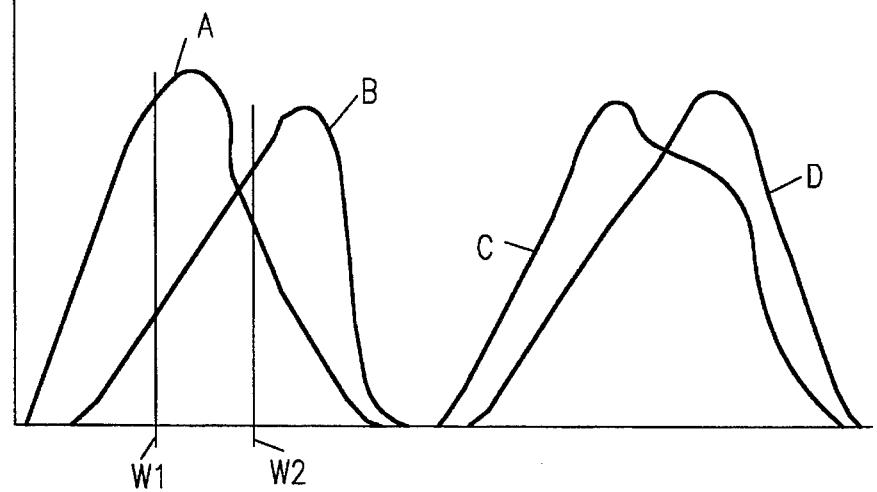
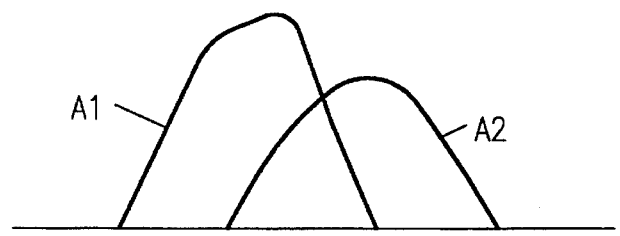
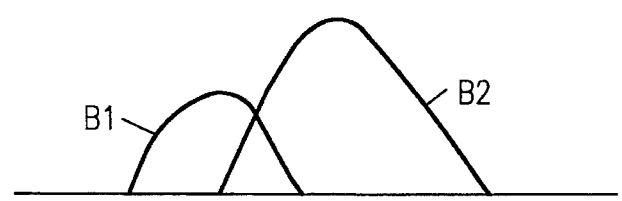
FIG. 14

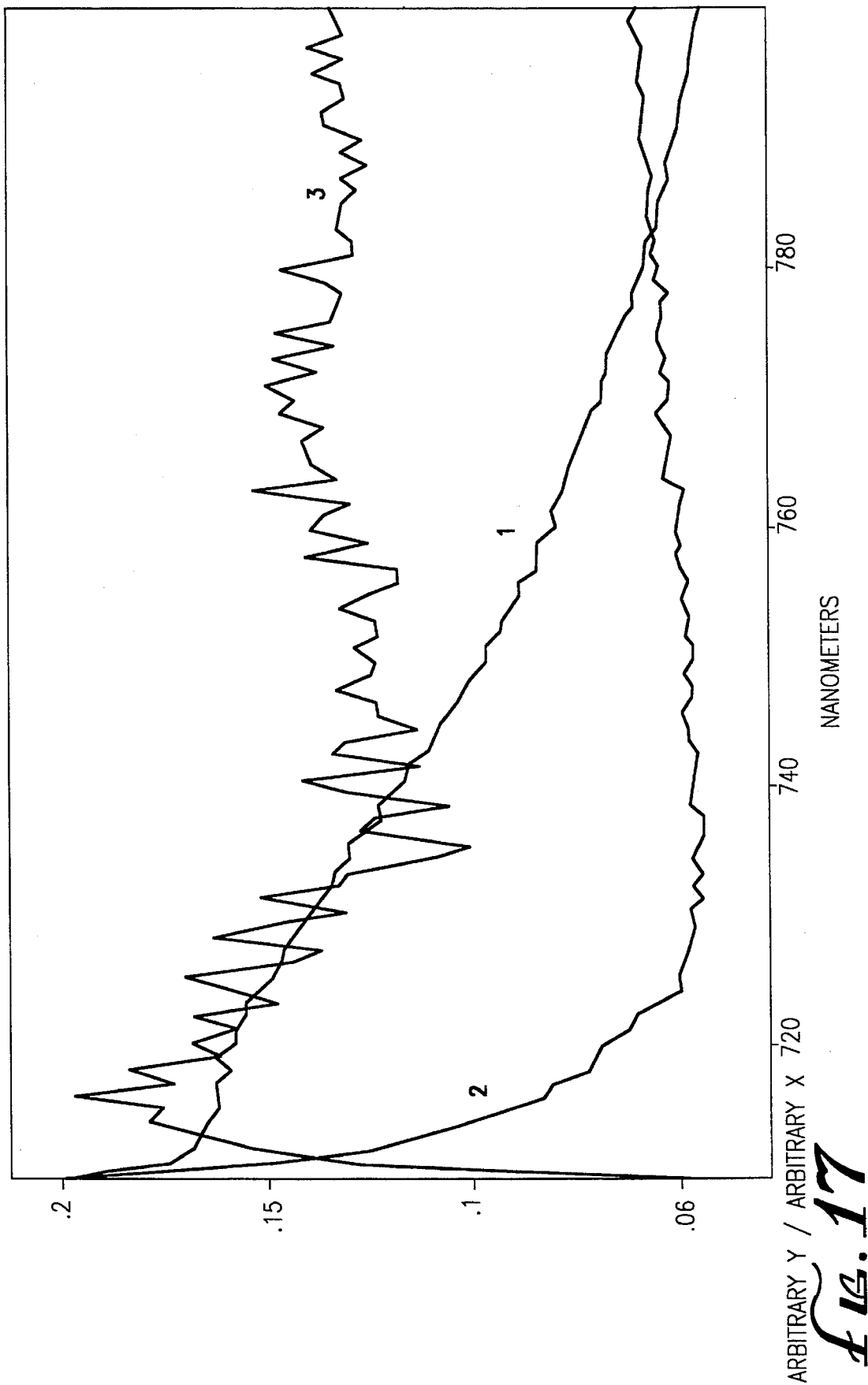

SIGNAL PROCESSING FOR CHEMICAL ANALYSIS OF SAMPLES

BACKGROUND

The present invention is directed to methods for analyzing chemical samples automatically with minimum manual involvement. Generally the less manual involvement, the less danger from toxic chemicals and the lower the cost of the analysis. The present invention is also directed to apparatus and method for improved sensitivity in obtaining information about chemical samples.

One type of automated analysis of a chemical sample is an "excitation" technique where the sample is subjected to an excitation input signal. Different compounds in the sample produce different output signals. The output signals are analyzed to identify or quantify the compounds in the sample emitting the output signals.

One method of analyzing an output signal is by comparing its wavelength with the wavelength of the excitation input signal generating the output signal. The output signal can include "non-resonant" and "resonant" signals. Where the wavelength of the output signal is substantially dependent on the wavelength of the input signal, the output signal is termed a "non-resonant" signal. Examples of such non-resonant signals are Rayleigh signals, Mie scattering, Brillouin scattering and/or Raman scattering. Where the wavelength of the output signal is substantially independent of the wavelength of the input signal, the output signal is termed a "resonant" signal. Examples of such resonant signals are fluorescence and phosphorescence signals. A problem with existing excitation technique is that the resonant and non-resonant signals interfere with each other and can overlap in frequency. Therefore, it is not easily possible to distinguish between the resonant and non-resonant signals.

Another problem with the excitation technique results from scattering of the input signals. Such scattering can result from scattering of off-fundamental input signals and by inelastic scattering, for example, Raman scattering of water.

Therefore, there is a need for a method and apparatus to accurately determine the analyte content of a sample wherein the sample, when activated by an input signal, generates a resonant and a non-resonant signal.

SUMMARY

The present invention provides a method and apparatus that satisfies this need. According to the method, the analyte content of a sample is determined by generating first and second input signals and directing the input signals to the sample. The input signals differ in wavelength by at least 3 nanometers. Due to the interaction between the input signals and the sample, first and second output signals are generated. Each output signal comprises a resonant signal whose peak wavelength is substantially independent of the wavelength of the respective input signal, and a non-resonant output signal whose peak wavelength is dependent upon the wavelength of respective input signal. A detector is used to detect the two output signals, and by distinguishing the resonant output signals from the non-resonant output signals, data about the analyte content of the sample is determined. For example, principal components regression analysis or other multivariate quantitative analysis can be applied to the output signals, for the purpose of distinguishing between the resonant and non-resonant signals.

In an alternate version of the invention, rather than distinguishing resonant from non-resonant output signals, it is possible to distinguish resonant output signals from each other, or the non-resonant output signals from each other.

Examples of resonant output signals are those generated by fluorescent or phosphorescent indicators or analytes. When the analyte is fluorescent or phosphorescent, then the wavelengths of the input signals both need to be within the excitation spectrum of the fluorescent of phosphorescent molecule. "Excitation spectrum" is the wavelength at which there is significant absorption by a molecule and subsequent emission of a photon from the molecule. Preferably, the fluorescent or phosphorescent wavelengths of the two input signals are from about 5 to 40 nanometers apart, and more preferably from about 10 to about 30 nanometers apart.

In one version of the invention, the resonant output signals can be related, i.e., the respective spectrum of the output signals are constant in shape and the signals peak at about the same frequency. This is typically the situation with fluorescent emissions, where the spectrum shape and the output peak of a fluorescent compound is not dependent upon the particular wavelength of the input signal, as long as the input signal is within the excitation wavelength band.

A variety of techniques can be used to generate the input signals. For example, there can be a generator with two separate sources such as laser diodes operating at different wavelengths, guided to the sample using, for example, a fiberoptic wave guide. The signals can be modulated by using a liquid crystal filter or any wavelength modulating device.

When distinguishing the components of the output signal, it is possible to use an Eigenvector for representing each of the four output signals (first and second resonant output signals and first and second non-resonant output signals). In a case where the resonant output signals are related i.e. have the same spectra with substantially the same peak output, it is possible to represent the two resonant output signals with a single Eigenvector.

This invention is also directed to an apparatus for practicing this method. In the apparatus, a signal generator is used for generating the input signals, with a guide being provided for directing the input signals to the sample.

The present invention has significant advantages. To analyze a sample, it is only necessary to excite it with two input signals. Multiple samples are not required. Thus, the method is quick and efficient. A small amount of sample preparation time is required as well as a small amount of time for the actual analysis. In effect, through the use of multiple input signals, the need to use multiple samples is eliminated. Further, by being able to subject a sample to multiple excitation input signals through, for example, electronic switching between different input signals, an efficient system is provided.

DRAWINGS

These and other features, aspects and advantages of the present invention will become understood with reference to the following description, appended claims and accompanying drawings where:

FIG. 13 is a flow chart for quantitative analysis by PCR in the time domain using fast Fourier transform (FFT) and truncation;

FIG. 14 is a representation of the fluorescence emission response in a multiplexed system where there are two fluorophores in a sample which is excited at two different wavelengths W1 and W2.

FIG. 17 are three eigenvectors extracted from the data sets of FIGS. 15 and 16;

DESCRIPTION

Detection Apparatus

Figure 1:
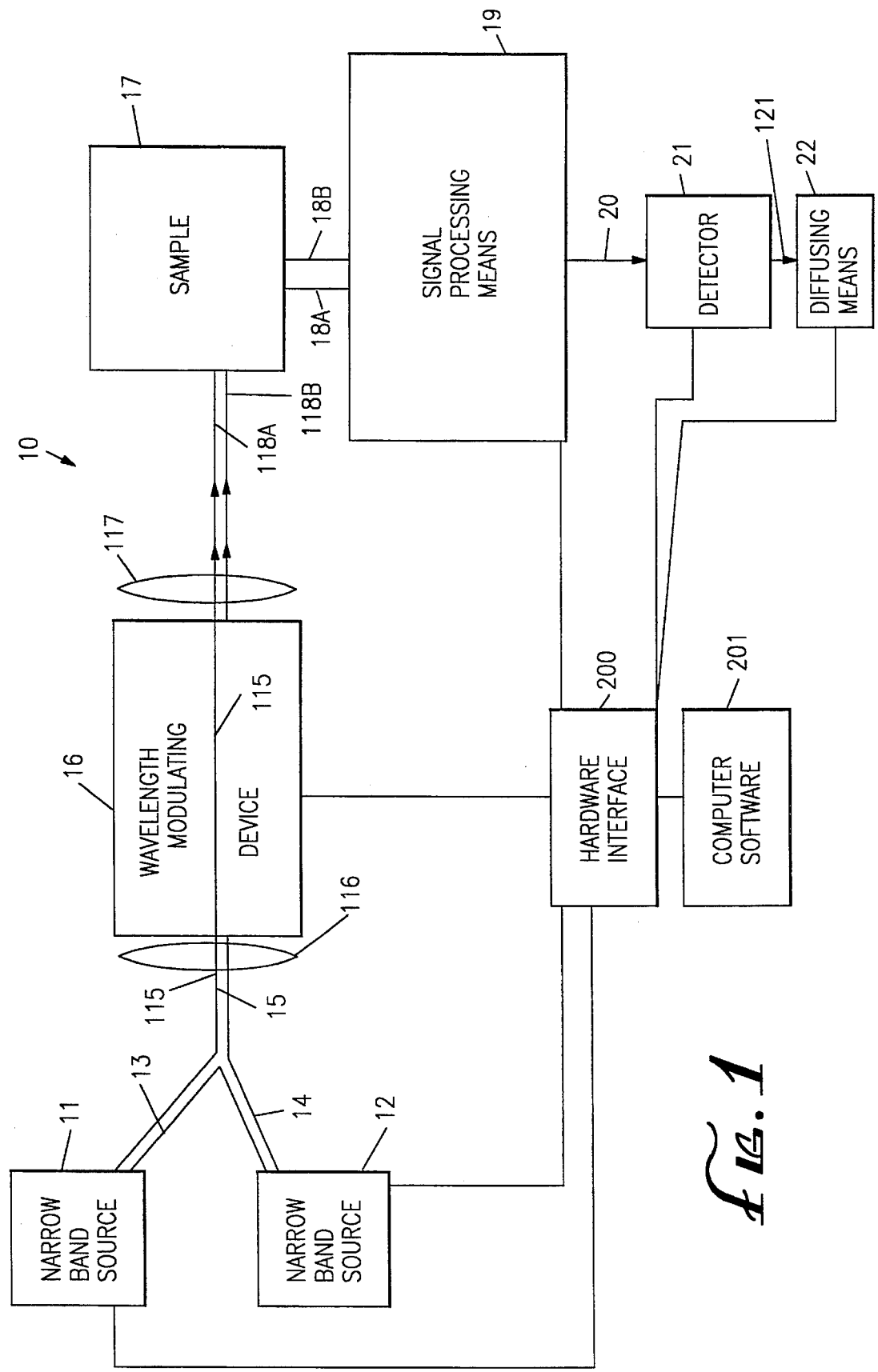
FIG. 1 is a block diagram representing the components of a system according to the present invention for analyzing a chemical sample.

Referring to FIG. 1, a spectroscopic analyzer 10 includes two narrow band sources 11 and 12 for generating two excitation input signals. The sources 11 and 12 can be laser diodes each operating to provide a laser signal at one of two selected wavelengths.

The signals from the sources 11 and 12 are directed along first fiber optic waveguides 13 and 14. The fiber optic waveguides 13 and 14 can be part of a bifurcated fiber optic waveguide 15 so that the input signals are directed along the joined fiber optic waveguide 15. Other techniques for obtaining the signals from each of the sources 11 and 12 can be used, such as a dichroic mirror or switching reflecting mirror. Furthermore, a beam splitter can be used to direct the signals instead of the fiber optic waveguides 13 and 14.

From the end of the fiber optic waveguide 15 the signal is directed to a lens 116 for collimating a signal 115 which is directed into a wavelength modulating device 16.

The wavelength modulating device 16 can be a liquid crystal filter or a mechanically switched filter. The modulating device 16 effectively acts to pass each of the two wavelengths from the sources 11 and 12 for further processing. From the modulating device 16 the signal 115 is directed to a focusing lens 117. A first focused input signal 18a at a first wavelength and a second focused input signal at a second wavelength 118b interact with a sample 17 containing an analyte. The sample 17 is capable of emitting two output signals, namely a first output signal 18a and a second output signal 18b corresponding to the two excitation input signals 118a and 118b, respectively, as a consequence of the interaction.

The output signals 18a and 18b from the sample 17 are directed along a path transverse to the path of the input signals 118a and 118b. This transverse path is preferably used where the output signals 18a and 18b are resonant signals, such as phosphorescent or fluorescent signals. This is preferred to limit the amount of light from the excitation input signal reaching the detector.

The output signals 18a and 18b from the sample 17 are passed through a signal processor 19, which can include a filter, dispersing element and/or monochromator. Output signals from the signal processor 19 are directed along a path 20 to a detector 21. From the detector 21, the signals are directed along a path 121 to a distinguishing means 22 for distinguishing and analyzing the output signals 18a and 18b. The distinguishing means 22 can be a multivariate analysis package.

The sources 11 and 12, the wavelength modulating device 16, the signal processing means 19, and the detector 21 are connected to a hardware interface 200. The interface 200 is connected to a computer 201 which typically includes the distinguishing means 22 software, a printer, a display, a terminal, memory and a microprocessor. The interface 200 is operated by a user to activate the interface components and obtain the processed data as necessary from the distinguishing means 22.

Each input signal to the sample has an intensity level, and the sample has an excitation coefficient. Preferably, the mathematical product of the intensity of the input signal at wavelength W1, and the excitation coefficient of the sample at wavelength W1, should be approximately equal to the corresponding mathematical product at wavelength W2 and any other W's used in the invention. If this is done, then the intensity of the output signals resulting from the input signals are about equal. This results in the wavelengths of the lasers 11 and 12, W1 and W2 respectively, being selected and controlled to maximize instrument sensitivity.

A single wavelength-tunable laser for each of the sources 11 and 12 is preferred to minimize the number of optical elements in the system. In some cases, a single laser tunable to the two different wavelengths can be used to provide the two signals at the two wavelengths. In the near infrared range, an effective approach is to use one diode laser. An alternative approach, as illustrated, is to use rapid selection from between two or more discrete diodes 11 and 12, each lasing at different wavelengths. Multiple input signals at multiple wavelengths can be obtained from multiple-tunable or fixed lasers, namely discrete lasers.

When tunable lasers are used, components of the spectrum at wavelengths longer than the fundamental wavelength are removed with an optical filter, such as the modulating device 16. This is necessary to minimize the amount of extraneous signals to be removed by the distinguishing means 22.

Filters in the processor 19 reduce scattered light at the excitation wavelength, and pass light of longer wavelengths. This avoids saturation of the detector 21, and minimizes the amount of rejection of the scattered light that needs to be effected by the distinguishing means 22.

Modulation of Input Signals

Modulation of the excitation laser sources 11 and 12 requires changing the filters continuously during measurements. This mechanical optical task can be complex. To avoid mechanical switching of filters, a ferroelectric liquid crystal device acts as a modulator 16. The device 16 electronically adapts the filters to the excitation wavelength in synchrony with the wavelength modulation.

A liquid crystal filter of the preferred kind is obtainable from the University of Colorado and is disclosed in the following U.S. Pat. Nos.: 5,132,826, "FLC Tunable Filters and Color Generation"; 5,231,527, "Chiral Smectic Liquid Crystal Polarization Interference Filters"; 5,243,455, "Improved Chiral Smectic Liquid Crystal Polarization Interference Filters"; and U.S. patent application Ser. No. 08/1062585 filed on May 17, 1993, "Split-Element Liquid Crystal Tunable Optical Filter". The contents of these patents and the patent application are incorporated by reference herein.

When the analyte in the sample is fluorescent or phosphorescent, the two wavelengths W1 and W2, which are different, are both in the excitation spectrum of the molecule. The "excitation spectrum" is where there is a significant absorption by a molecule in a sample leading to a subsequent emission of a photon. The difference between W1 and W2 is at least 3 nanometers and typically from about 5 to about 40 nanometers, and preferably from about 10 to about 30 nanometers. When there are two or more lasers, this difference in wavelengths is accomplished by electronic modulation in the device 16 rather than by mechanically switching filters and/or monochromators. The ferroelectric liquid crystal device of the modulating device 16 permits for rapid modulation and provides freedom from mechanically variable filters.

In an alternative arrangement, where a rapidly switching laser is used to provide the two input signals with different wavelengths, filters are still needed.

Output Signals: Distinguishing the Signals

The output emission signals 18a and 18b (at the respective first and second input wavelengths W1 and W2) are used to construct at least part of an Excitation emission Matrix (EEM) to distinguish between the output signals.

The ability to extract quantitative information from small excitation wavelength shifts results from the use of principal component regression analysis. Such a technique separates the spectral components of non-resonant output signals which vary with shifts in input wavelength, from spectral components of resonant output signals which are substantially constant and independent of input wavelength variations within the resonant signal's excitation spectrum. Once separated, these signals can then be rejected or retained in the quantitative model.

The first output signal 18a is generated by the interaction of the first input signal 118a at the first wavelength W1 with the sample 17. The second output signal 18b is generated by the interaction of the second input signal 118b at the second wavelength W2 with the sample 17.

Figure 6A:
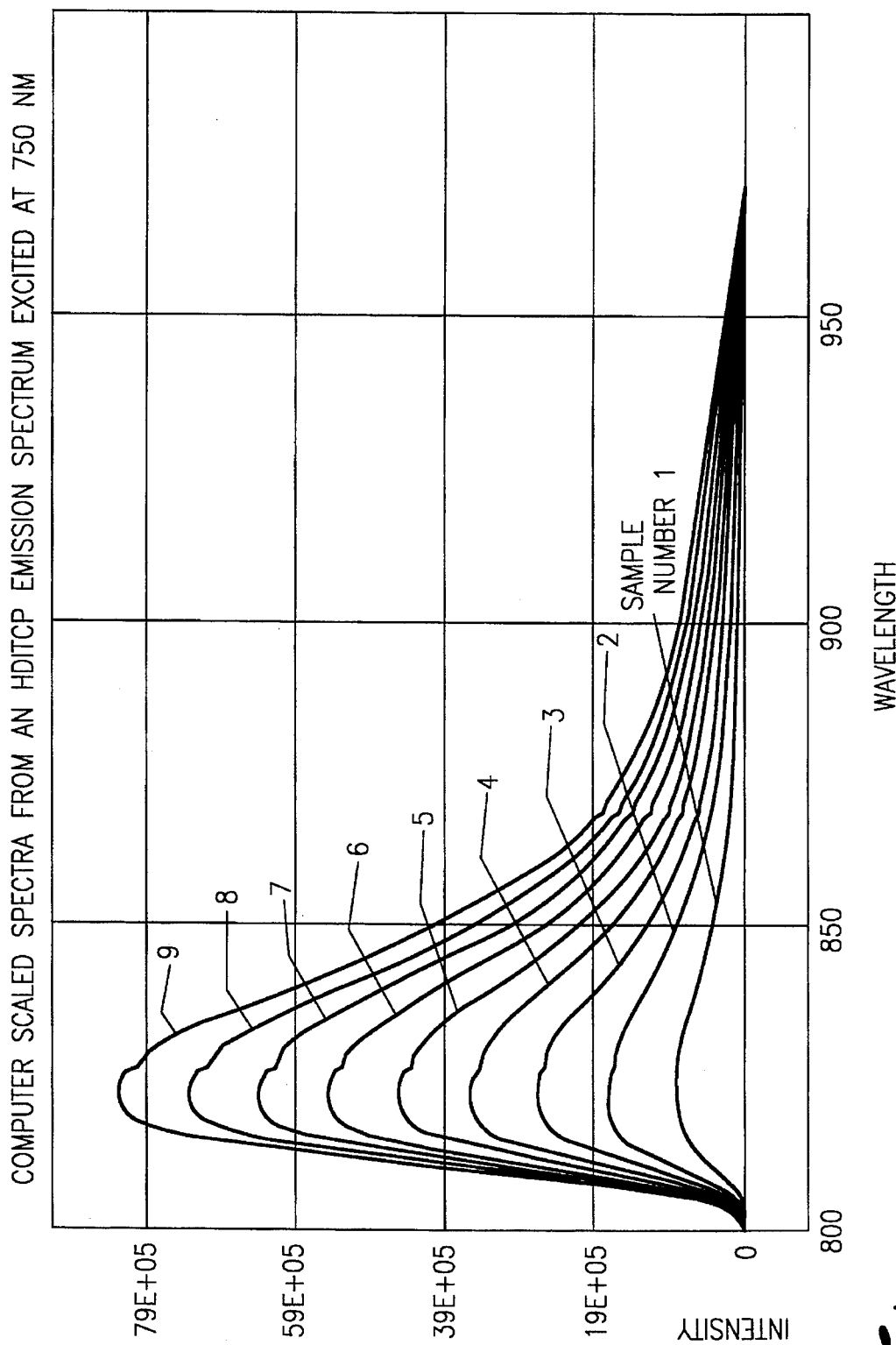
FIGS. 6A and 6B are spectra generated by scaling an HDITCP (1,1',3,3',3'-hexamethyl-4,4',5,5,-dibenzo-2,2'-indotricarbocyanine perchlorate, Kodak laser grade) emission spectrum.
Figure 6B:
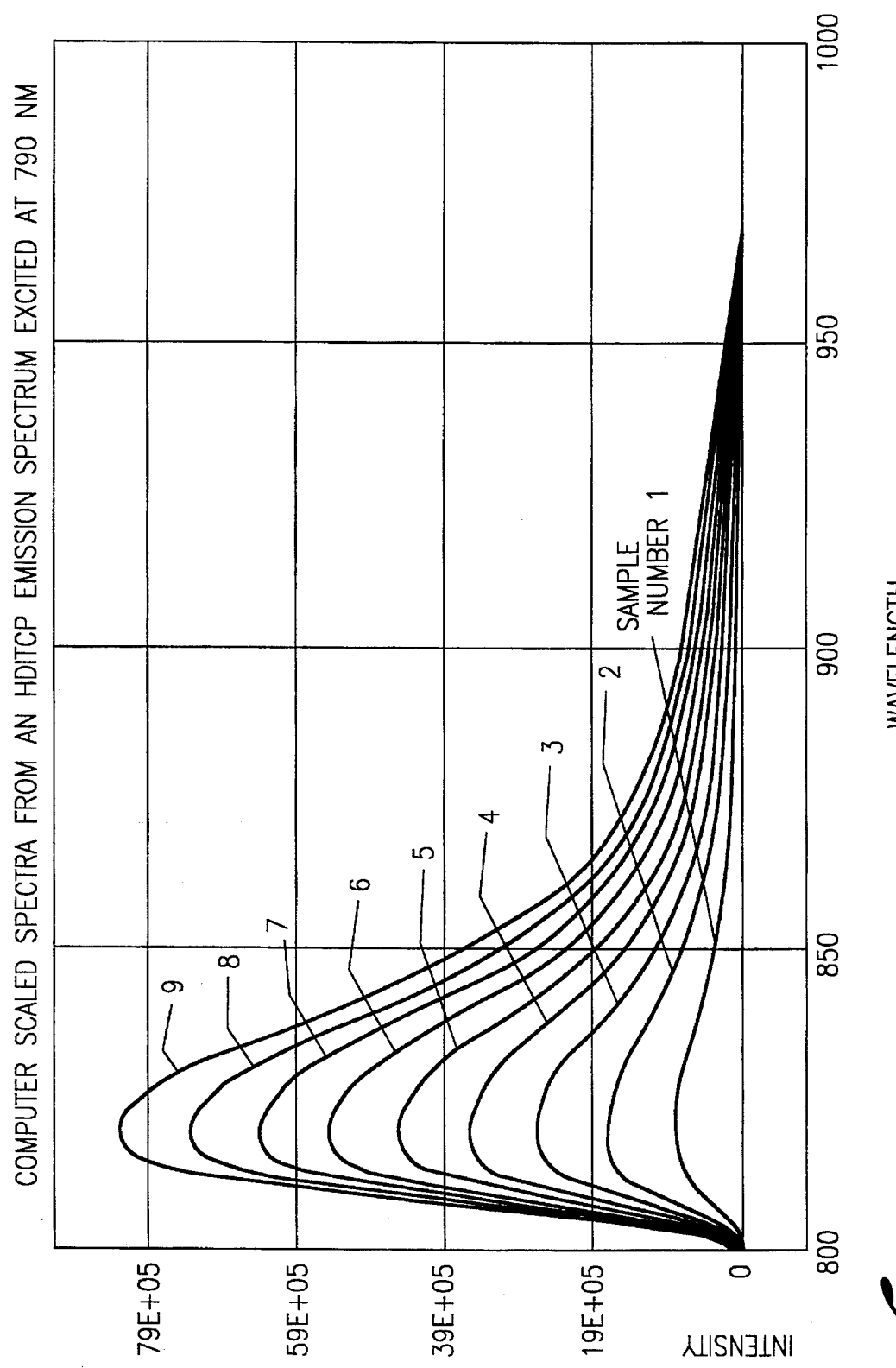

In order to obtain characteristics of the sample 17, different concentrations of the sample 17 are subjected to the same input signals 118a and 118b at wavelengths W1 and W2. Different output signals 18a and 18b for each concentration are measured. A representation of these different spectra for different dye concentrations is illustrated in FIGS. 6A and 6B and is discussed further below.

Typically the first output signal 18a comprises (i) a first resonant output signal whose peak wavelength is substantially independent of the wavelength W1 of the first input signal 118a and (ii) a first non-resonant output signal whose peak wavelength is dependent upon the wavelength W1 of the first input signal 118a. The second output signal comprises: (i) a second resonant output signal whose peak wavelength is substantially independent of the wavelength W2 of the second input signal 118b, and (ii) a second non-resonant output signal whose peak wavelength is dependent on the wavelength W2 of the second input signal 118b. The distinguishing means 22 acts to distinguish between the resonant output signals and the non-resonant output signals.

Figure 2:
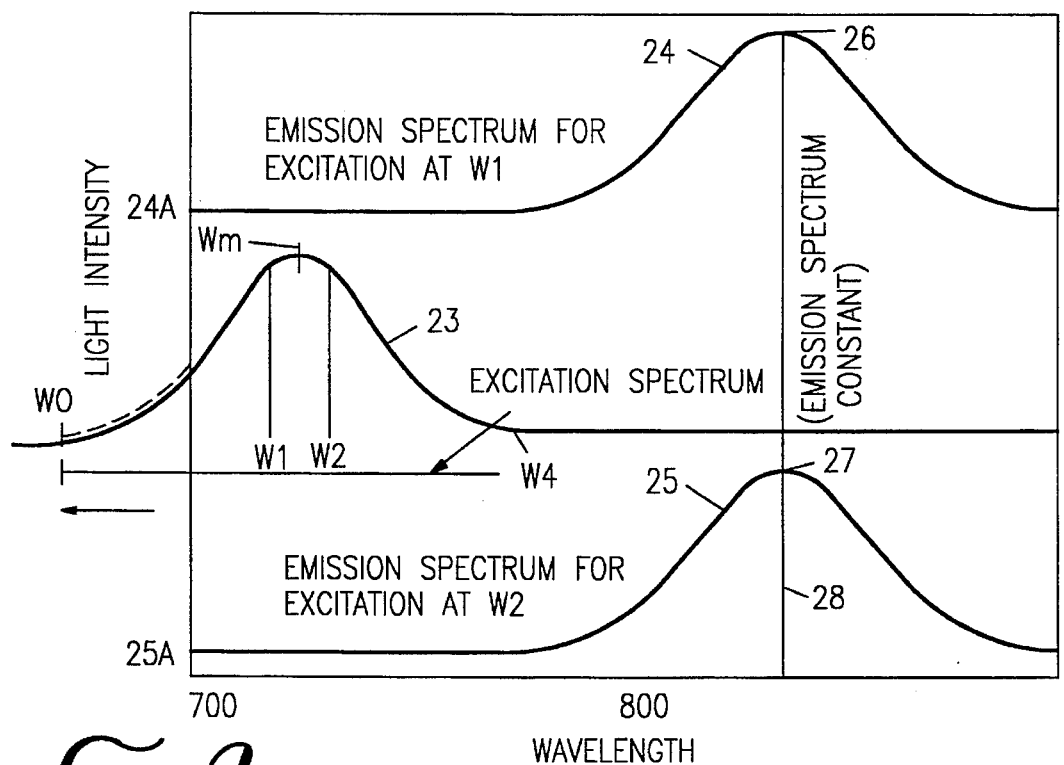
FIG. 2 is a graphical representation of the fluorescence emission response of a sample in relation to excitation wavelength at two wavelengths, W1 and W2.

FIG. 2 illustrates a spectral diagram relating to a spectroscopic analysis to determine fluorescence illustrating an aspect of the invention wherein the output signals comprise resonance output signals. In FIG. 2, the excitation spectrum is defined as wavelengths between W0 and W4. The wavelengths of the resonance signals are governed by the electronic transitions of the emitting molecules of the sample 17.

Input signals

In the spectroscopic process to determine fluorescence, there are provided at least two input signals 118a and 118b to generate the output signals 18a and 18b from the sample 17. The input signals 118a and 118b, as originating from the source diodes 11 and 12 and processed by the modulating device 16, have a selected excitation wavelength varied from W1 to W2. This range is within a excitation spectrum defined as wavelength between W0 to W4. Wm represents the maximum excitation wavelength.

If the wavelength of the input signals 118a and 118b were less than that of W0 or greater than that of W4, then there would be insignificant absorption by a molecule in the sample 17. Accordingly, there would be insignificant subsequent emission of photons from the molecule.

The analyte in the sample 17 has an absorption level, and the laser source has one or more power levels. The wavelengths W1 and W2 are preferably selected such that the mathematical product of the laser power level and the analyte absorption level is the same at the first and at the second wavelengths, W1 and W2, respectively.

W1 and W2 can both be on one side, for example, the lower side of Wm, or on both sides of Wm (shown in FIG. 2). The range W1 to W2 lies in the neighborhood of the excitation maximum to obtain a maximum fluorescence response i.e. the maximum emission within the excitation spectrum.

The excitation spectrum 23 is diagrammatically illustrated in FIG. 2 between W0 and W4. The first input signal 118a is centered about the first wavelength W1, and the second input signal 118b is centered about the second wavelength W2.

The Spectra of Resonant Output Signals

The first output signal 18a comprises a first resonant output signal 24 having an emission spectrum 24a, and the second output signal 18b comprises a second resonant output signal 25 having an emission spectrum 25a. In the embodiment discussed in FIG. 2 the resonant output signals are fluorescence signals.

The output signals 24 and 25 are "related" because their emission spectra, 24a and 25a, respectively, are constant in shape, and the signals and 25 peak at about the same frequency. Even if the respective amplitudes of the signals 24 and 25 are different, the signals are still related due to their constant shape, irrespective of amplitude.

As can be seen in FIG. 2, the shapes of the emission spectra 24a and 25a are constant and centered about the same wavelength, as indicated by line 28.

The signals 24 and 25 can vary in amplitude. This is indicated by the peak 26 for the first quantitative signal 24 at W1 (FIG. 2). The peak 27 for the second quantitative signal 25 at W2 is less than the peak intensity 26. In other embodiments of the invention, the peaks 26, 27 can be equal, or the peak 27 can be higher than peak 26. The relative value of intensity does not impact the desired data to be determined by the distinguishing means 22 so long as the intensity values are workably related in the same intensity range, normally less than about 1000:1.

Although FIG. 2 shows two input signals at W1 and W2 and two output signals having a spectrum about the same wavelength indicated by line 28, it is possible to have multiple input signals at multiple different wavelengths as appropriate. Thus there can be input signals W1, WM, and W2 if it were desired to have three output signals with the same spectra.

Also, if the wavelengths W1 to W2 vary, the emission spectra of the output signals remains at a maximum centered about line 28. The intensities, for example, as indicated by numerals 26 and 27 vary with wavelength from W1 to W2. Effectively, the curves 24 and 25 representing the different emission spectra at different input wavelengths W1 to W2 move vertically. The curves are centered about line 28, and the emission spectra are constant; that is, the spectra would have a similar shape similar to the depicted output signals 24 and 25.

In distinguishing resonant output signals from each other, the spectra of the resonant output signals are compared. Referring to FIG. 14, input signals have different excitation wavelengths W1 and W2 and the output signals have different emission spectra. A first output spectrum A includes first component spectral curves $A_1$ and $A_2$. A second output spectrum B includes second component spectral curves $B_1$ and $B_2$. These first component and second component waves are related as illustrated in FIG. 14. As such, curve $A_1$ is related to curve $B_1$, and curve $A_2$ is related to curve $B_2$. The combination of the spectra A and B for a first resonant signal is a curve C. The combination of the spectra A and B for a second resonant signal is a curve D.

The different resonant signals can be distinguished because the excitation wavelengths of different resonant output signals differ although the signals themselves have related emission spectra.

The Spectra of Non-resonant Output Signals

Figure 3:
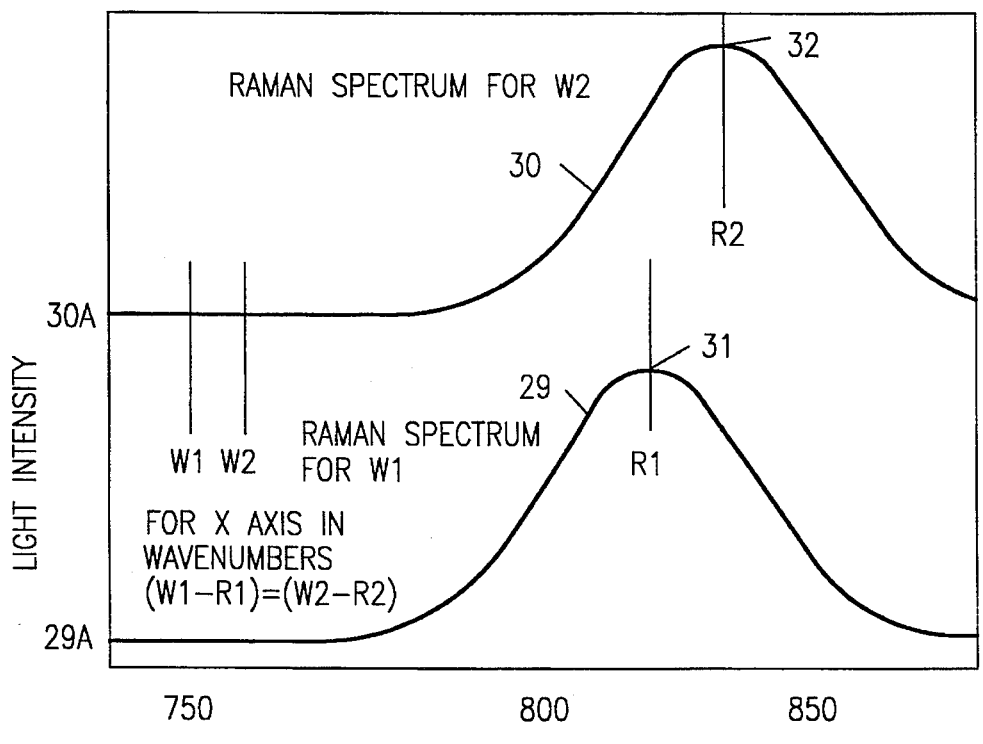
FIG. 3 is a graphical representation of a Raman scattering output of a sample in response to signals at two wavelengths, W1 and W2.
Figure 4:
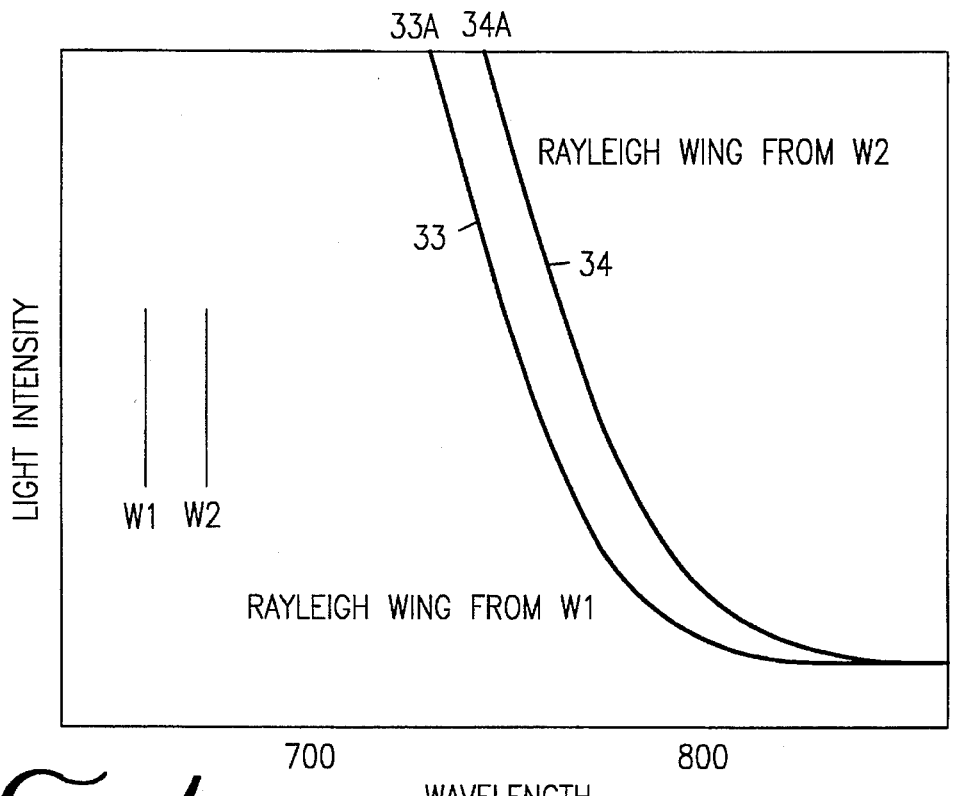
FIG. 4 is a graphical representation of a Rayleigh "wing" output of a sample in response to input signals at two wavelengths, W1 and W2.

FIGS. 3 and 4 illustrate spectral diagrams relating to a spectroscopic analysis where the output signals comprise non-resonant output signals. The input signals and the excitation spectrum are not illustrated. Wavelengths W1 and W2 represent the wavelengths of the two input signals. The criteria for the input signals is similar to that described with reference to FIG. 2.

Raman Scattering (FIG. 3)

In the embodiment described in FIG. 3, the first output signal 18a comprises a non-resonant output signal 29 having an emission spectrum 29a, and the second output signal 18b comprises a non-resonant output signal 30 having an emission spectrum 30a.

The output signals 29 and 30 are "unrelated" because their emission spectra, 29a and 30a, respectively, are non-constant in shape, and move in position depending on the wavelength of the input signals.

The non-resonant output signals 29 and 30 comprise Raman signals having the Raman spectra 29a and 30a respectively. The spectrum 29a has an intensity peak 31 at a spectral position R1, and the spectrum 30a has an intensity peak 32 at a spectral position R2.

The wavelength of an output Raman signal varies in a predictable manner corresponding to variations in input signal wavelength, as shown in FIG. 3.

With a shift of input wavelength from W1 to W2, the spectral position R1 of the spectrum 29a shifts to the spectral position R2 of the spectrum 30a. This shift from R1 to R2 is indicative of the unrelated output signals 29 and 30. The exact location of the Raman peaks 31 and 32 depends on both the inelasticity of the scattering center which determines the Raman shift, and the excitation wavelengths W1 and W2 which determine the reference from which the scattering light is shifted. The spectrum of the first and second non-resonant output signals 29 and 30 are, thus, not substantially constant or similar, and therefore the signals are not related.

Rayleigh Scattering (FIG. 4)

The wavelength at which Rayleigh scattering occurs is also dependent upon the excitation wavelength as illustrated in FIG. 4. In fluorescence spectroscopy, this Rayleigh scattering, or background, signal component is generally seen as a negatively sloping baseline or wing.

In the embodiment described in FIG. 4, the two input signals 18a and 18b are centered about wavelengths W1 and W2, respectively. The first output signal 18a comprises a non-resonant output signal 33 having an emission spectrum, or wing, 33a, and the second output signal 18b comprises a non-resonant output signal 34 having an emission spectrum, or wing, 34a.

The output signals 33 and 34 are unrelated because their emission spectra, 33a and 34a, respectively, are non-constant in shape, and move in position depending on the wavelength of the input signals.

Figure 5:
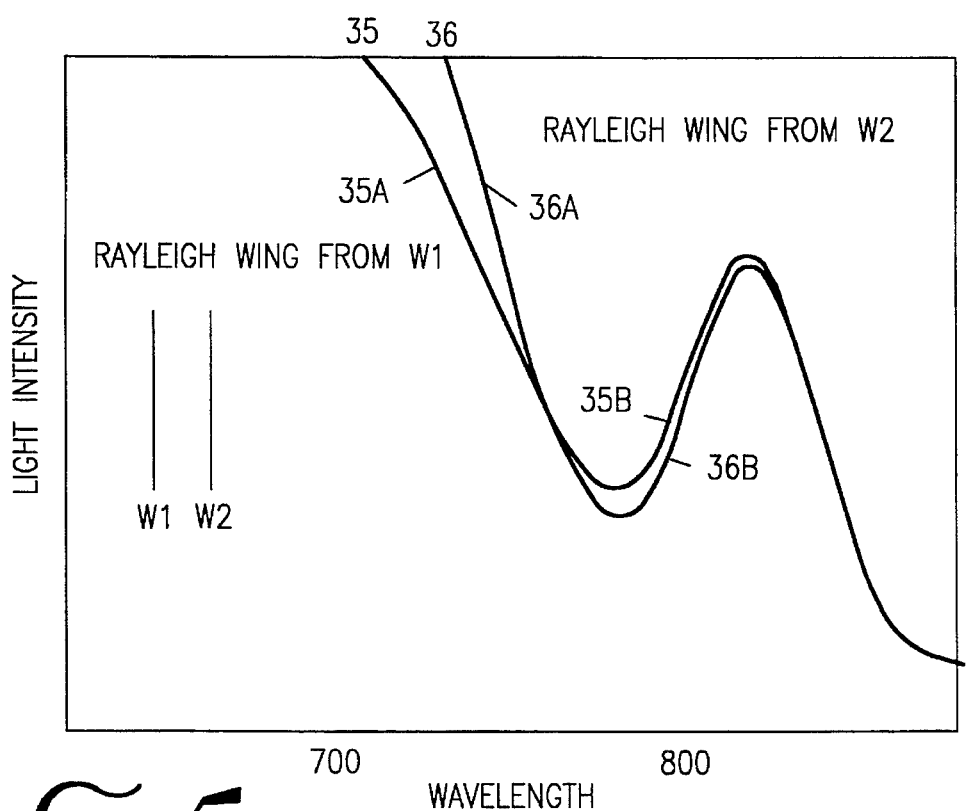
FIG. 5 is a graphical representation of an emission spectrum of a sample generating both fluorescence and Rayleigh scatter upon modulation of the excitation wavelength at two wavelengths, W1 and W2.

Output Signals with Rayleigh Scattering and Fluorescence Signals (FIG. 5)

FIG. 5 is an illustration of the spectra for both Rayleigh and fluorescence output signals. In the embodiment described in FIG. 5, the two input signals 18a and 18b are centered about wavelengths W1 and W2, respectively. The first output signal 18a comprises a first Rayleigh output signal 35a and a first fluorescence output signal 35b, and the second output signal comprises a second Rayleigh 36a output signal and a second fluorescence output signal 36b. The first and the second output signals are represented by the spectra 35 and 36 respectively. The spectra 35 and 36 represent spectra containing both the fluorescence signals, 35b and 36b, which are related, and Rayleigh signals, 35a and 36a, which are unrelated.

Signal Processing For Distinguishing Output Signals

The distinguishing means 22 separates the output signals 18a and 18b obtained from detector 21 into their component signals based on their output characteristics. Processing the output signals includes principal components analysis of the emission spectra of the output signals.

Referring to FIG. 2, the first resonant output signal comprises a first fluorescent signal 24 having a first spectrum 24a. The second resonant output signal comprises a second fluorescent signal 25 having a second spectrum 25a. The first and the second spectra 24a and 25a are constant, and as such, the first and the second fluorescent output signals 24 and 25 are related. The spectra are shown as a linear combination in a single spectrum. The spectra may be defined by one Eigenvector representing the emission spectrum of a fluorophore compound in the sample 17. A single coefficient is used to quantify and provide a measure of any changes in the overall emission intensity of the fluorophore.

Referring to FIG. 3, the first non-resonant output signal comprises a first Raman scattering 29 having a first spectrum 29a. The second non-resonant output signal comprises a second Raman scattering 30 having a second spectrum 30a. The non-resonant output signals can also comprise Rayliegh signals as shown in FIG. 4.

The emission spectra of Raman scattering is shown in FIG. 3, and the emission spectra of Rayleigh signals are shown in FIG. 4. The emission spectra 29a and 30a of Raman scattering in FIG. 3 do not have a constant spectral shape, and therefore, the signals are unrelated. Thus, they cannot be expressed in terms of a single eigenvector. Similarly, the emission spectra of Rayleigh signals in FIG. 4 cannot be expressed in terms of a single eigenvector.

The difference between the spectral shapes of resonant and non-resonant signals, described above, is separable by principal components regression analysis of data from a single sample taken by varying the excitation wavelength between W1 and W2. Other techniques of multivariate analysis such as partial least squares can also be utilized.

The emission data sets corresponding to excitation at W1 and at W2 containing both fluorescence and scattering signals, such as Rayleigh scattering, are processed by use of a multi-variate model. In such a model, the quantitation is based on eigenvectors which do not depend on the excitation wavelength. In this manner the scattering signals, namely the unrelated output signals, are excluded from the quantitative model, namely related signals such as resonant signals.

Multivariate Quantitative Analysis

The data representative of the output signals obtained from the detector 21 is processed in the distinguishing means 22 to separate the output signals 18a and 18b into their components based on their characteristics. The processing of the output signals 18a and 18b includes multivariate quantitative analysis.

This analysis can include the pretreatment of data representing the output signals, calibration of the detection apparatus, and the quantitative measurement of properties of unknown samples.

Processing and computations can be effected with a LabCalc® spectroscopy software package (Version A2.22, Galactic Industries Corporation, Salem, N.H.). Spectral retrieval, storage, manipulation and display of the data, as well as the ability to process arrays and vectors representative of the data are possible with this program. Many other software programs are available to perform the spectral analysis. For instance, there are quantitative analysis packages from Nicolet (Nicolet in Madison, Wis.), Perkin-Elmer (Norwalk, Conn.), Digilab and Pirovette (Infometrix of Seattle, Wash.). The spectral analysis procedures are well known, and are described, for example, in *Factor Analysis & Chemistry* by Malinowski and Howery (Wiley-Interscience 1980). The contents of this reference are incorporated by reference herein.

The analysis of the data and its effect on the data are briefly reviewed.

Pretreatment of the Data

Multivariate models achieve calibration empirically by correlating data gathered from standard samples with known values of the desired analytical properties for these standards.

Fourier transformation enhances both quantitative precision and speed with which processing is carried out. Fourier transformation of a finite, non-periodic function, namely a spectrum, is a useful pretreatment technique for the data for multivariate quantitative analysis. Such transformation preserves a unique and valid representation of all quantitative information of the original data. The Fourier transform is a linear transformation and preserves the frequency and magnitude data points in a linear relation to analyte concentrations similar to conventional absorbance or intensity units. Spectra of condensed phase materials in the ultra violet (UV), visible, near infrared and infrared regions of the spectrum are shown by Fourier analysis to retain most of their useful quantitative information in signal components which change relatively slowly with wavelength. Detector noise, source fluctuations, and other interferences which often change more rapidly are isolated by discrimination.

Other techniques can be used as a pretreatment or prefiltration step for the data. In this connection, a moving average technique such as a Savitzky-Golay filter can be used for the removal of high frequency noise. However, such a filter generally does not reduce the number of data points to the extent possible with the Fourier technique. More information on the pretreatment of data is set out in U.S. Pat. No. 4,660,151 (Chipman). The contents of that patent are incorporated by reference herein.

The pretreatment effectively reduces the amount of redundant data and noise in the signal. In the context of the present invention such pretreatment is optional.

Multivariate Processing

Experimental data representing the output signals 18a and 18b can be processed in the distinguishing means 22 by any one or more of classical least squares, inverse least squares, principal component regression, and partial least squares.

The data is processed both in a time domain and as raw spectra. As a measure of accuracy of each technique, the Standard Error of Estimate (SEE) and Standard Error of Prediction (SEP) are determined.

An inverse least squares method is based on the classical least squares method. A single matrix inversion is required during the calibration step and no constraints are placed on the number of components, wavelengths, or mixtures used in the calculations. Inverse least squares minimizes variance in concentration.

Spectroscopic measurements have some uncertainty. If the predominant uncertainty is not in the in the spectroscopic data, then the inverse least squares method is preferred. Otherwise, the classical least squares method is preferred. The fewer matrix inversions required by the inverse least squares approach tend to outweigh the potential benefits of a change in coordinates during the regression steps. Inverse least squares is the preferred method because of greater resistance to problems with near singular matrices.

The problems of matrix singularity in multiple linear regression determinations is reduced by using orthogonalization methods. This is an eigenvector analysis by singular value decomposition, or factor analysis. An orthogonal matrix is one where all the column vectors are mutually perpendicular. Orthogonalization of a matrix prior to an inverse least squares method permits inversion of the matrix without singularity problems. This technique is principal component regression. This technique is also known as P-matrix method, target transform factor analysis or target factor analysis.

Orthogonalization of a matrix prior to classical least squares also permits determination of an unknown matrix without singularity problems. A second orthogonalization process is required to permit prediction of unknown concentrations when a first matrix is not square.

The number of eigenvectors used in the principal component regression calculations is that which yields the lowest Standard Error of Prediction values with a particular data set. The eigenvectors are determined empirically for each combination of data set and pretreatment method. Increasing numbers of eigenvectors in the basis set lowers the Standard Error of Estimate since there are more degrees of freedom used in the model.

Removing Noise and Background Scattering

In general, preprocessing or pretreatment of the data is helpful if the analytical data contains signal components which have random spectral characteristics, such as noise, scattering by randomly-sized particles in suspension, or randomly occurring contaminants. Different techniques are possible for pre-treating and processing the data to obtain the requisite resonant and related output signals.

Figure 10:
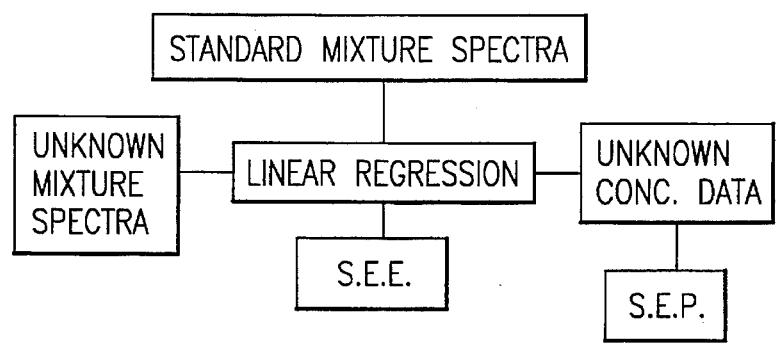
FIG. 10 is a "K-matrix" namely a classical least squares, calibration using a least squares linear regression scheme.

In FIG. 10, a scheme for analysis of emission spectra is shown. A two-wavelength classical linear regression (Classical Least Squares or K-matrix) calibration is used in which the maximum intensity of each emission peak, corrected for baseline, is fit to concentration. There is no pretreatment of the data in this example.

Figure 11:
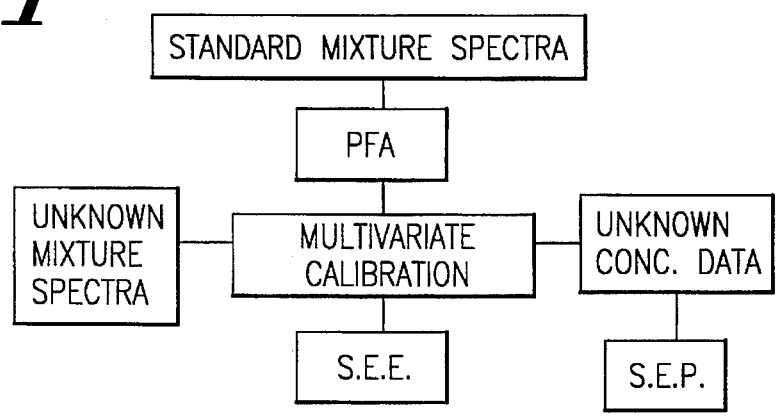
FIG. 11 is a full-spectrum quantitative analysis by factor analysis (PFA) and inverse least squares calibration (ILS) on the eigenvector representation of each spectrum.

FIG. 11 illustrates a full-spectrum calibration using Principal Component Regression analysis. There is no pretreatment of the data in this example.

Figure 12:
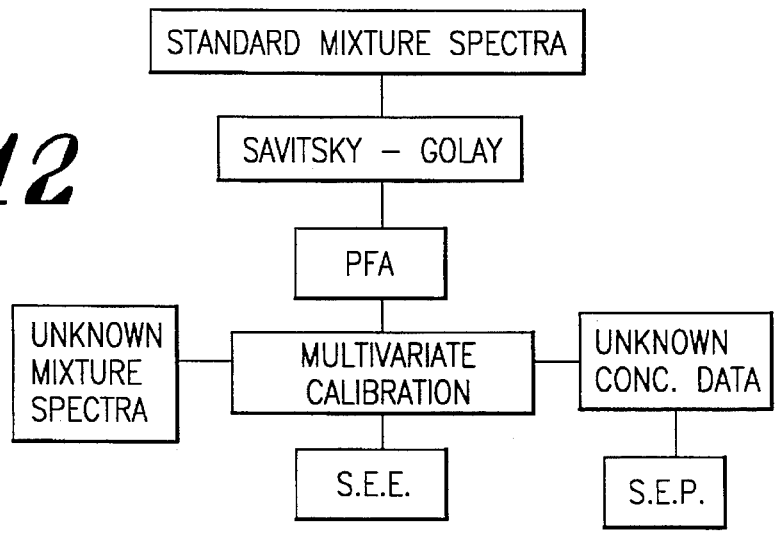
FIG. 12 is a flow chart for quantitative analysis by principal components regression (PCR) with pretreatment or pre-filtration by Savitzky-Golay smoothing.

FIG. 12 illustrates a full-spectrum analysis of data which is smoothed or pre-treated by a Savitzky-Golay algorithm, in which intensity at wavelength is replaced by a weighted mean of the measured intensities at wavelengths.

The use of Savitzky-Golay smoothing is sufficient to remove high-frequency noise. Expressing the data as a truncated Fourier series offers additional advantages of superior data compression and the ability to discriminate low-frequency background components.

FIG. 13 illustrates Principal Component Regression analysis of the data in the time domain, with a Fast Fourier transform to pretreat the data.

The four quantitative models illustrated in FIGS. 10 to 13, when applied to fluorescence emission spectra having no significant spectral overlap or interference, report similar standard errors.

Where there is little noise in the data the various preprocessing or pre-treating procedures are relatively closely related. Where there is a greater degree of spectral overlap and interfering signal components, resulting, for instance, from Rayleigh scattering and from energy transfer, multivariate methods are able to resolve interferences even where there is no preprocessing or pretreatment of the data.

Where the spectral shape of background signals is consistent, and merely varies in magnitude from sample to sample, the use of factor analysis and target transformation can permit resolution of signal from background, provided that the set of standard mixtures is sufficiently extensive to reveal the independence of the background from the signal levels.

Examples

Figure 7:
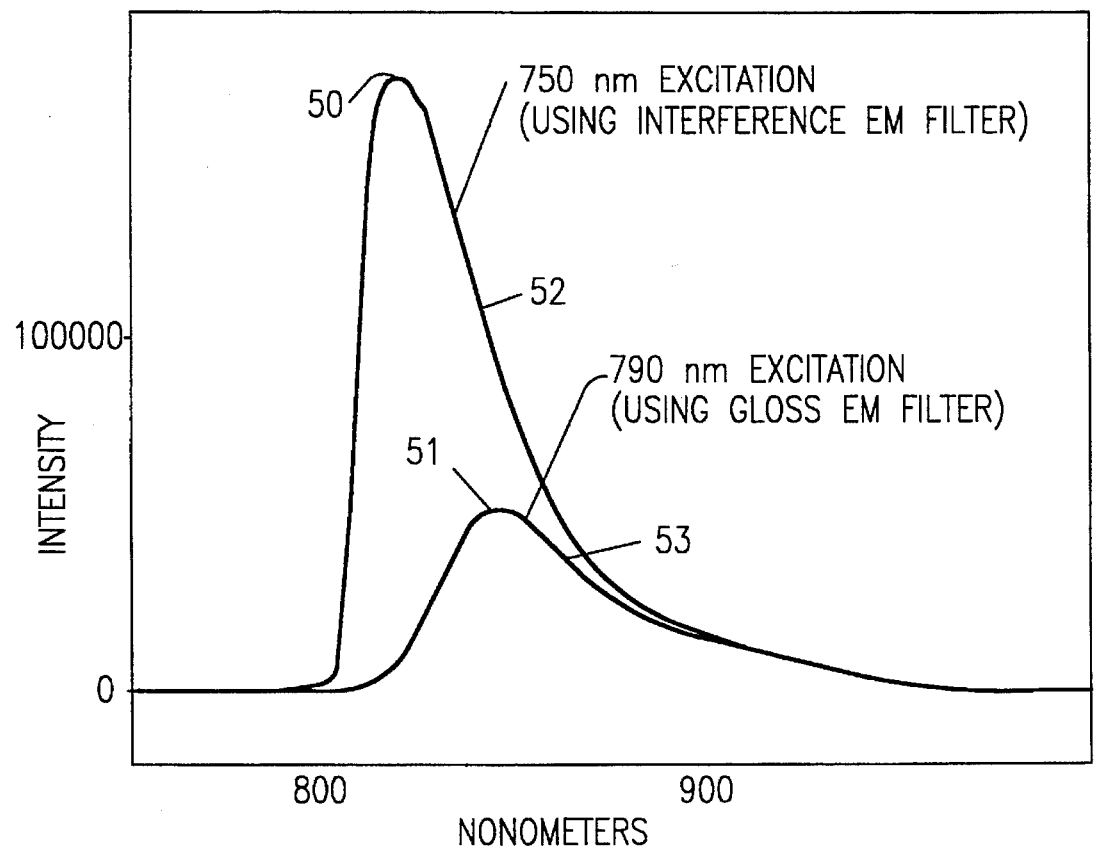
FIG. 7 is an emission spectra from an HDITCP fluorophore excited at two different wavelengths, where peak wavelengths shift due to a change in emission filters.

Example 1. (FIGS. 6A, 6B and 7)

Emission spectra were obtained using 750 nm diode laser excitation of the near infrared fluorophore HDITCP (1,1',3,3',3'-hexamethyl-4,4',5,5'-dibenzo-2,2,indotricarbocyanine perchlorate, Kodak laser grade) to obtain changes in spectral amplitude for a series of samples scaled to nine different dye concentrations. This is illustrated in FIG. 6A which shows the spectra generated by scaling HDITCP emission spectrum after a sample excitation at a 750 nm wavelength. These spectra indicate output signals which are associated because their spectra vary uniformly with analyte concentration. "Associated" signals are two or more apparently different output signals which vary with the concentration of analyte in a uniform and/or predictable manner.

A similar series of spectra were developed for a 790 nm excitation wavelength, and are illustrated in FIG. 6B. These spectra also indicate output signals which are associated because their spectra vary uniformly with analyte concentration.

The scaled spectra were then each combined by vector addition with background spectra obtained using 50 and 790 nm excitation, as appropriate. The signal-to-background ratio of the data, as well as the concentration, were manipulated independently to give an analyte concentration range of one decade.

Each of the scaled spectra were given a random "white" noise component equal to 1% of the spectrum's signal magnitude to simulate uncertainty with real measurements.

The scaled noise-added data were subjected to multivariate analysis by principal components regression using Lab-Calc® BASIC program modules. (Galactic Industries, N.H.) Using as metrics the computed standard error of prediction (SEP) and standard error of estimate (SEE), the data were analyzed to determine deconvolving excitation-modulated fluorescence data via multivariate computation, and the number of significant component vectors required to perform such work.

The scaled spectra had a very high signal to noise ratio. Unscaled background spectra with peak intensities of about $10^{-4}$ were added to those of the fluorescence signals. The added background components were not significant relative to the fluorescence signals, and did not pose a challenge to the deconvolution process.

FIG. 7 is a representation of two emission spectra of a single sample. This figure is representative of one spectrum 52 of the series from FIG. 6A at 750 nm excitation, and one spectrum 53 of a series from spectra of excitation at 790 nm from FIG. 6B.

Two different emission filters were used in the generation of 750 nm excited and 790 nm excited fluorescence signals 52 and 53 respectively. The emission peaks 50 and 51 of the respective emission spectra 52 and 53 do not have a unique shape common to both data sets. The spectra were convoluted by the filters to differing degrees depending upon the excitation wavelengths as indicated in FIG. 7.

The spectra generated by scaling the data in FIG. 7 were analyzed to reveal that good (< 2% error) quantitation is possible where the shape of the emission spectrum is dependent upon the excitation wavelength.

Two eigenvectors were used in the analysis. The first eigenvector is the mean of the 750 nm and 790 nm emission spectra. The second, a bipolar eigenvector, represented the apparent shift in peak emission in moving from 750 to 790 nm.

Quantitation can be performed on excitation wavelength modulated data when the emission spectra are not of a constant shape, but vary uniformly with concentration. This arises where emission filters are multiplexed in synchrony with the excitation wavelength to avoid saturation of the detector with a scattering peak.

Thus, deconvolution of quantitative information of resonant signals from non-resonant signals, such as light scattering, is obtainable using the multivariate analysis.

Example 2. (FIGS. 8 and 9)

A set of scaled spectra were generated for HDITCP using 750 and 790 nanometer excitation with the same interference filters in the emission channel for all measurements. In this experiment, the background spectra were scaled up by the necessary factor ($10^4$) to give a signal-to-background ratio of approximately unity for the lowest fluor "concentration." The scaled background was added to the scaled fluorescence spectrum, and "white" noise was added to the resulting sum to simulate experimental measurement uncertainties and avoid the occurrence of singularities which would result if mathematically perfect data were supplied.

Figure 8:
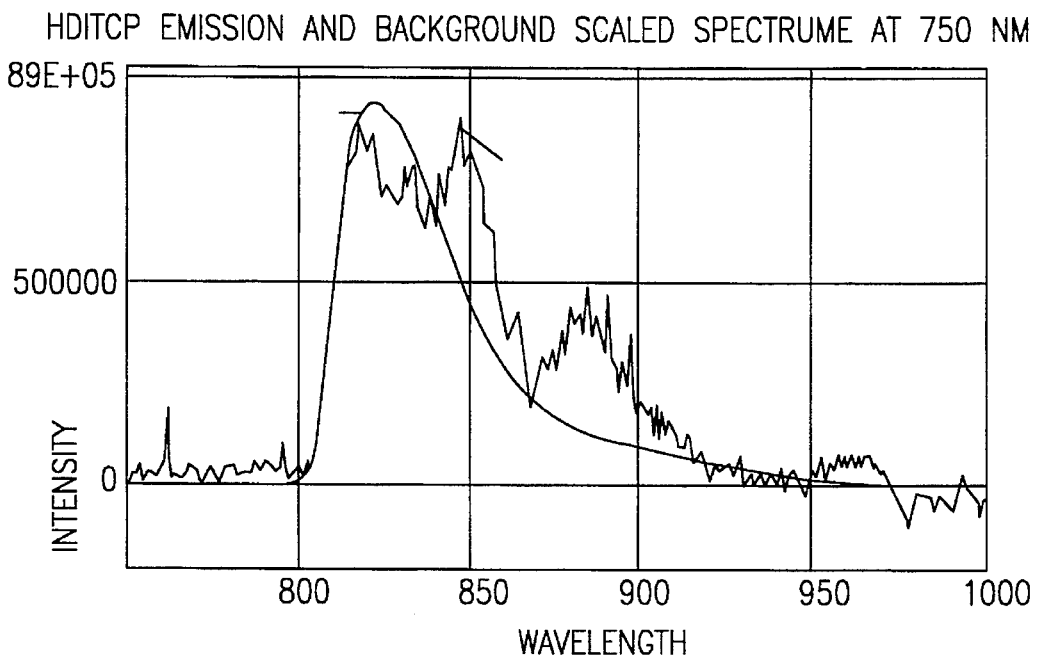
FIG. 8 is a background spectrum from 750 nm excitation of a sample HDITCP, the spectrum being multiplied in intensity to be equivalent in intensity to a spectrum from a fluor well above background in signal intensity.
Figure 9:
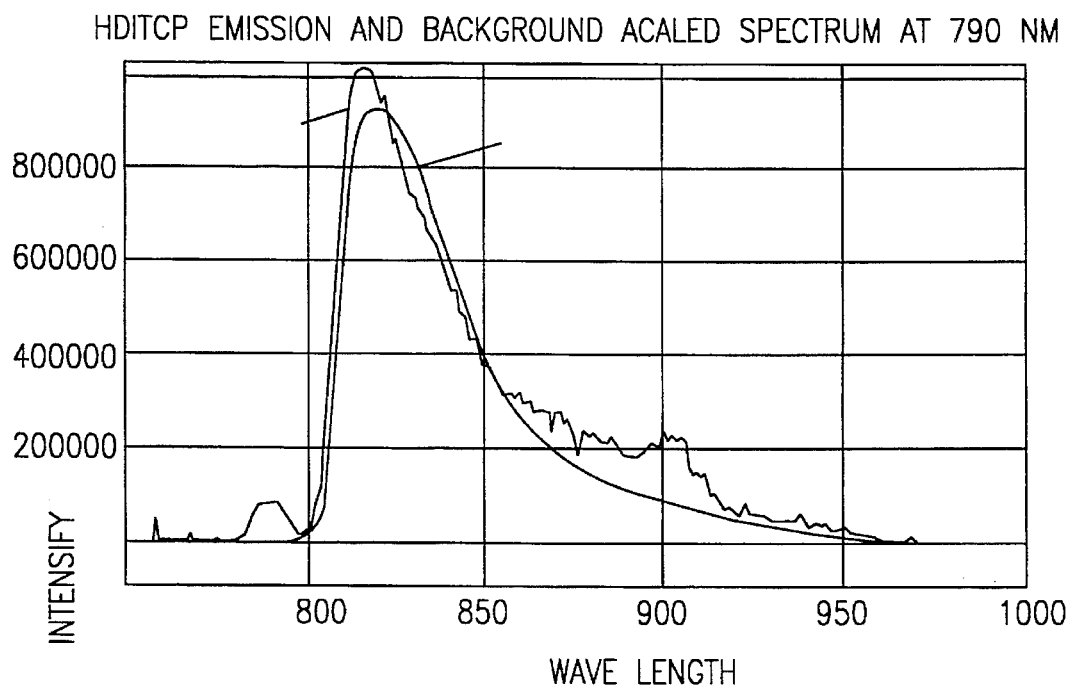
FIG. 9 is a background spectrum from 790 nm excitation of a sample HDITCP, the spectrum being multiplied in intensity to be equivalent in intensity to a spectrum from a fluor well above background in signal intensity.

The smooth spectra in FIGS. 8 and 9 represent fluorescence. The fluorescence spectra have a common peak shape regardless of the excitation wavelength. The irregular lines in FIGS. 8 and 9 represent background Mie and Raman output spectra.

Multivariate analysis resolves resonant signals such as fluorescence from non-resonant signals such as Raman and Mie signals. Eigenvectors were assigned to Raman and Mie signals and to fluorescent signals at each input signal wavelength. Thus, the eigenvectors were assigned to resonant signals (i.e. fluorescent) and to non-resonant signals (i.e. Raman and Mie). By such assignment and an application of multivariate analysis, the non-resonant signals were distinguished.

Five eigenvectors were required to model the system for the fluorescence and background data. The percent error for the unknowns was approximately 7%. The increase in number of eigenvectors from 2 to 5 result from the lower signal to background ratio. This requires additional degrees of freedom to account for the 750 nm and 790 nm backgrounds and elastic scattering of both 750 nm and 790 nm light into the detector, in addition to the fluorescence signal itself.

Synchronous modulation of both source wavelength and emission filter passbands yield data resolvable from background non-resonant signals.

A system can be used where there is a time-dependent wavelength sensitivity introduced into the emission channel to suppress scattered light and conserve detector dynamic range. By adding one or more additional eigenvectors to the basis set, the desired quantitative information may be extracted from the data.

Example 3

Solutions of the NIR fluor IR144-propanediamine (IR144-PDA) were prepared ranging in concentration from $10^{-8}$ to $10^{-9}$ M (Table 1). The solvent for these samples was neat Beckman APO control serum, reconstituted from its lyophilized form. This matrix is moderately turbid and generates background signals which are dependent upon the excitation wavelength used, and which are comparable in magnitude to the fluorescence from IR144-PDA at the concentrations chosen. The samples were excited by the output of a 450 watt xenon arc lamp after passage through the grating monochromator of an SLM-AMINCO SLM4800C instrument, using a slit chosen to give a FWHM of 16 nm. The center wavelength of the monochromator was set to either 680 or 690 nm to effect modulation of the excitation wavelength. Emissions from the sample were detected at a normal angle by the SLM4800C's Hammamatsu (Trademark) R928 photomultiplier, operated in current mode.

The resulting emission spectra were then uploaded to a network file server and converted to the proper format for analysis using modules written in the Array Basic language supported by Grams/386 (version 2.01A, level III, Galactic Industries, Salem N.H.). Multivariate analysis was performed using principal components regression.

TABLE 1

Data for IR144-PDA in APO control serum. "Concentration" is number of microliters of $10^9$M fluor per 0.5 ml of sample. Shaded cells are training set). Excitation waves 680 nm and 690 nm respectively.

| Fluor Concentration | Filename for 680 Excitation | Filename for 690 Excitation |
| --- | --- | --- |
| 500 | SLM 15109 | SLM15108 |
| 400 | SLM15124 | SLM15125 |
| 350 | SLM15123 | SLM 15122 |
| 300 | SLM15120 | SLM15121 |
| 250 | SLM15119 | SLM15118 |
| 200 | SLM15116 | SLM15117 |
| 150 | SLM15115 | SLM15114 |
| 100 | SLM15112 | SLM15113 |
| ZERO BLANK | SLM 15111 | SLM15110 |

OBSERVATIONS

Eigenvector analysis of the data permitted the resolution of resonant signals from non-resonant background components and thereby improved the quantitative precision of the analytical model.

Figure 15:
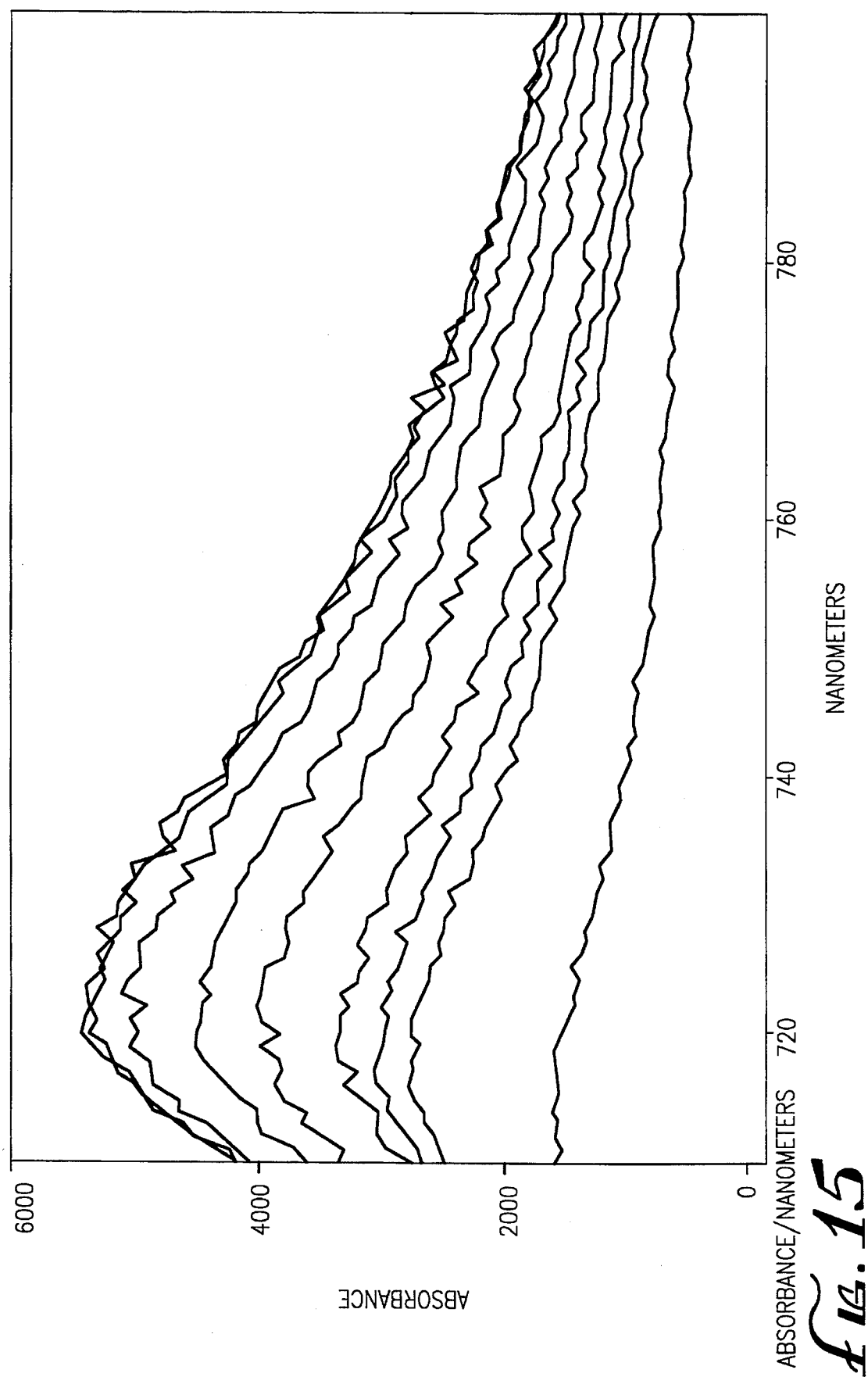
FIG. 15 is a graphical representation of emission spectrum of different fluor concentrations at 680 nm.
Figure 16:
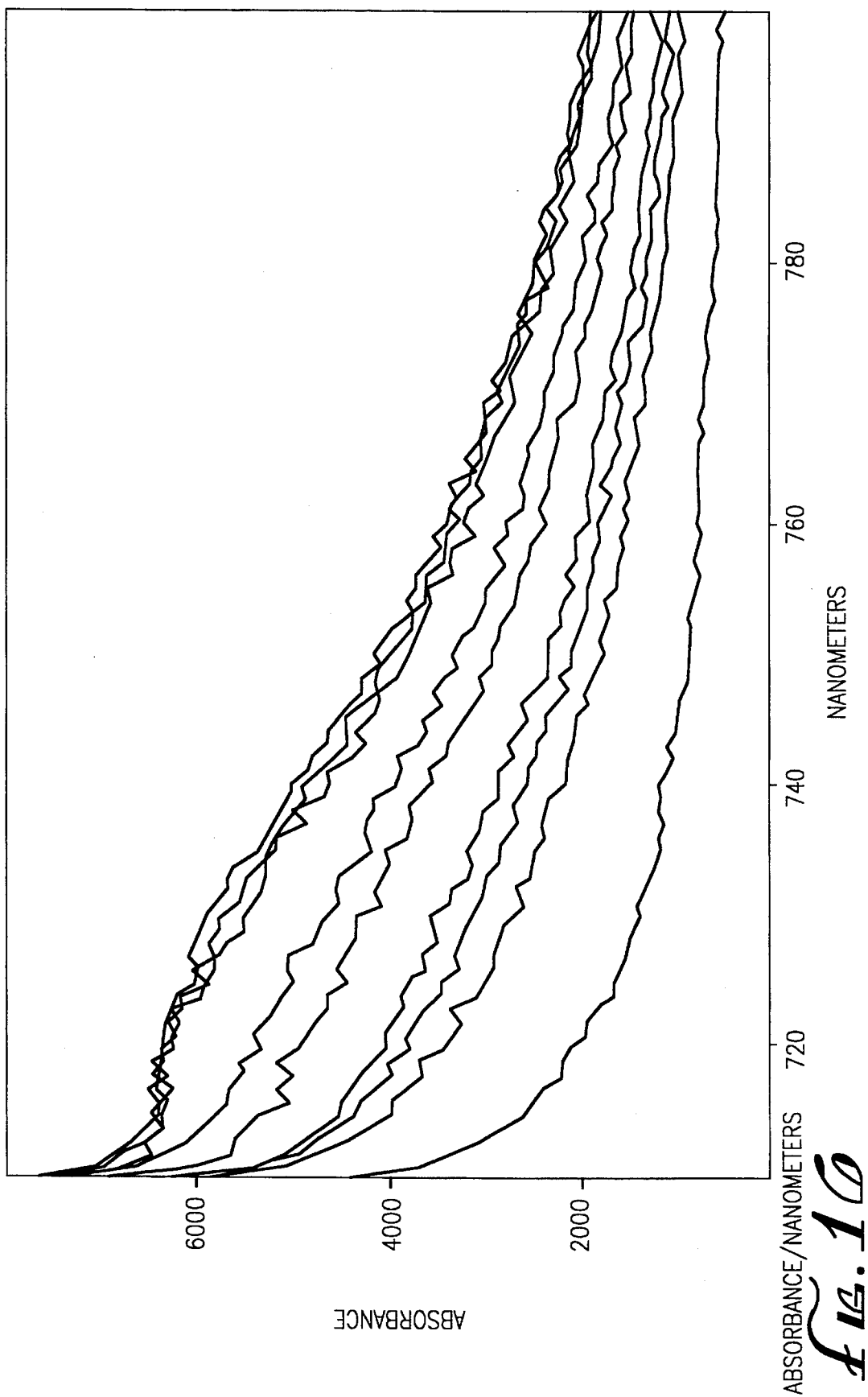
FIG. 16 is a graphical representation of emission spectrum of different fluor concentrations at 690 nm.

The original data is shown in FIGS. 15 and 16, for 680 nm and 690 nm excitation, respectively. It is apparent in the data that a scattering signal is present when using 690 nm excitation, which is located at 710 nm and longer wavelengths. When the excitation is moved to 680 nm, the scattering signal is much less pronounced, because of the greater separation between the excitation and emission wavelengths.

FIG. 17 shows three eigenvectors, marked by numerals 1, 2 and 3, which result from factor analysis of a subset of the data chosen to comprise a "training set" (Table 1). For a discussion of training sets and other aspects of multivariate analysis, consult E. Malinowski "Factor Analysis in Chemistry", 2nd ed., Wiley Interscience, New York, USA, 1991. The first and second eigenvectors describe the (fluorescence+ background) and (background) signal components, respectively, and that linear combinations of these two vectors may be created in which the background signal is subtracted from the fluorescence data. Addition of the third eigenvector provides an additional degree of freedom which describes an additional background component present as a sharp "spike" near 710 nm. Factor analysis of the data suggests that three different signals are present in the experimental data, and that these signals sum to give the observed emission spectra. This is understandable if one considers that two distinct background are present in the data (taken as a whole)—these correspond to scattering and endogenous matrix fluorescence of the sample using an excitation wavelength of 680 nm, and a different background resulting from use of 690 nm. The label IR144-PDA, however, produces a constant emission spectrum which is unchanged in shape by the excitation wavelength modulation, and so contributes only one eigenvector, for a total of three eigenvectors which span the data set.

Quantitative models of the data based on Principal Components Regression (Principal Component Regression) on the reduced eigenvector basis given in FIG. 17 generally reveal that the concentration of the fluor in a mixture may be computed from an unknown spectrum by application of Principal Component Regression prediction to both the 680 and 690 nm excited emission spectra and then taking the mean of the computed concentrations for each spectrum (Table 2). Only three eigenvectors are required for this level of precision.

2. The resulting multivariate quantitative model exhibits excellent background rejection characteristics and is able to predict fluor concentrations from emission spectra excited at either 680 nm or 690 nm.

3. When the excitation wavelength changes from 680 to 690 nm, there are produced two unrelated background spectra and two related fluorescence spectra from the desired analyte. In the eigenvector analysis, the two unrelated signals do indeed give rise to two independent eigenvectors, while the two related fluorescence spectra, having the same shape, give a single eigenvector for a total of three.

Variations of The Invention

Many other forms of the invention exist, each differing from others in matters of detail only. For example:

A. Although the description is based on input signals having two wavelengths, there could be more than two discrete wavelengths applicable to more than two input signals.

B. Instead of laser sources for the system, a broad band excitation source can be used, for instance, an arc lamp, a laser pump acoustic optic tunable filter, or a tungsten lamp.

C. The system is operable in a frequency range at least in the near infrared region and the visible region. As illustrated in FIGS. 2, 3 and 4 the ranges disclosed there are between about 700 to 850 nanometers. Signals in the broader frequency range could be processed similarly to those described in the detailed embodiments.

D. The detection method and apparatus can be applied to any appropriate detection system, for instance, spectroscopic systems, and chromatographic systems. By having to prepare and analyze less samples to obtain the necessary sample information, relative to prior art systems, the invention provides a significant advance over known detection methods and apparatus.

Among the analytes the system can be used for are fluorescent compounds and phosphorescent compounds and any known methodologies where these type of compounds are used as labels or probes, e.g., DNA hybridization assays and lummunoassays.

TABLE 2

Results of applying multivariate quantitative model (Principal Component Regression) to the analysis of data presented in FIG. 1.

| FILENAME | EXPECTED CONC. | COMPUTED CONC. (680) | COMPUTED CONC. (690) | MEAN CONC. | PERCENT ERROR |
|---|---|---|---|---|---|
| SLM15120 SLM15121 | 300 | 296 | 287 | 291.5 | 2.9% |
| SLM15116 SLM15117 | 200 | 190 | 175 | 182.5 | 8.7% |
| SLM15112 SLM15113 | 100 | 112 | 89.0 | 100.8 | 0.8% |

These examples support the following conclusions:

1. Data has been generated using IR144propanediamine and control serum which shows the ability of principal component regression to resolve resonant and non-resonant signals from a set of emission spectra obtained by varying the excitation wavelength.

The above embodiments of the invention are only a few possible examples of the apparatus and method of the present invention. It is to be understood that the present invention is not limited to operation in accordance with the embodiments discussed in this description, and that one skilled in the art would readily understand how to modify the invention to obtain equivalent results without departing from the spirit and scope of the invention. The invention is to be determined solely by the following claims.

What is claimed is:

1. Apparatus for determining the analyte content of a sample, the apparatus comprising:
   (a) a signal generator for generating a first input signal having a first wavelength, and a second input signal having a second wavelength, the two wavelengths differing by at least about 3 nanometers;
   (b) a means for directing the first and second input signals to a sample containing an analyte to generate, respectively, a first output signal and a second output signal due to interactions between the input signals and the analyte,
   wherein the first output signal comprises: (i) a first resonant output signal whose peak wavelength is substantially independent of the wavelength of the first input signal and (ii) a first non-resonant output signal whose peak wavelength is dependent upon the wavelength of the first input signal, and
   wherein the second output signal comprises: (i) a second resonant output signal whose peak wavelength is substantially independent of the wavelength of the second input signal, and (ii) a second non-resonant output signal whose peak wavelength is dependent on the wavelength of the second input signal;
   (c) a detector for detecting the first and second output signals; and
   (d) means for distinguishing the resonant output signals from the non-resonant output signals to obtain data about the analyte content of the sample.

2. An apparatus as claimed in claim 1 wherein the signal generator comprises: (i) two separate sources, each one for generating a source signal; (ii) a modulator for selectively directing the source signals to the sample as the input signals; and (iii) means for directing the source signals to the modulator.

3. Apparatus as claimed in claim 2 wherein the sources are laser diodes operative at different wavelengths.

4. An apparatus as claimed in claim 2 wherein the modulator comprises a wavelength modulating device and the means for directing the first and second input signals comprises a fiberoptic waveguide having a common waveguide and two limbs, each limb being directed to one of the sources, with the common waveguide being directed to the wavelength modulating device.

5. Apparatus as claimed in claim 4 wherein the wavelength modulating device is a liquid crystal filter.

6. Apparatus as claimed in claim 1 including processing means between the sample and the detector, the processing means including at least one of a filter, dispersing element and monochromator.

7. Apparatus as claimed in claim 6 wherein the processing means includes the filter, the dispersing element and the monochromator.

8. Apparatus as claimed in claim 1 wherein the resonant output signals are signals responsive to molecular emission, including at least one of a fluorescence or phosphorescence signal.

9. Apparatus as claimed in claim 1 wherein the non-resonant signals include at least one of a Rayleigh signal, Mie, Brillouin, and Raman scattering signal.

10. Apparatus as claimed in claim 1 wherein the signal generator generates input signals such that the first and second resonant output signals have substantially the same spectra.

11. Apparatus as claimed in claim 10 wherein the signal generator further comprises means for generating the first and the second input signals in sequence.

12. Apparatus as claimed in claim 1 wherein the means for distinguishing the output signals comprises means for expressing the first and the second resonant output signals as a single eigenvector, wherein the first and the second non-resonant output signals are not capable of being expressed as a single eigenvector.

13. Apparatus as claimed in claim 1 wherein the means for distinguishing the output signals comprises means for selecting a predetermined number of eigenvectors for expressing the first and the second resonant output signals.

14. Apparatus as claimed in claim 1 wherein the distinguishing means comprises means for applying principal components regression analysis to the first second output signals, whereby the resonant output signals are distinguished from the non-resonant output signals.

15. Apparatus as claimed in claim 1 wherein the distinguishing means comprises means for applying multivariate quantitative analysis to the first and second output signals, whereby the first and the second resonant output signals are distinguished from the first and the second non-resonant output signals.

16. Apparatus as claimed in claim 15 wherein the first and second input wavelengths are separated by about 3 nanometers to about 40 nanometers.

17. Apparatus as claimed in claim 14 wherein the first resonant output signal and the second resonant output signal have a first spectrum and a second spectrum respectively, and wherein the first non-resonant output signal and the second non-resonant output signal have a third spectrum and a fourth spectrum respectively, and
   wherein the signal generator generates input signals such that the first and the second spectra are substantially the same, and such that the third and the fourth spectra are different, and
   wherein the means for principal components regression analysis comprises (i) means for retaining the first and the second resonant output signals having the same spectra and (ii) means for rejecting the first and the second non-resonant output signals having different spectra.

18. Apparatus as claimed in claim 1 wherein the analyte has an absorption level, and wherein the generator has one or more power levels, and wherein the generator further comprises means for selecting the first and the second wavelengths such that the mathematical product of the generator power level and the analyte absorption level is the same at the first and at the second wavelengths respectively.

19. Apparatus as claimed in claim 1 wherein the signal generator generates the first and the second input signals in sequence, and wherein the first and the second non-resonant output signals comprise first and second Raman signals respectively, the first and the second Raman signals having a first and a second Raman spectrum respectively, and
   wherein the first Raman spectrum is at a first spectral position dependent on the first wavelength, and the second Raman spectrum is at a second spectral position dependent on the second wavelength, and wherein the first spectral position is different from the second spectral position.

20. Apparatus as claimed in claim 1 wherein the signal generator generates the first and the second input signals in sequence, and wherein the first and the second non-resonant output signals comprise first and second Rayleigh scattering signals respectively, the first and the second Rayleigh signals having a first and a second Rayleigh spectrum respectively, and wherein the first Rayleigh spectrum is at a first spectral position dependent on the first wavelength, and the second Rayleigh spectrum is at a second spectral position dependent on the second wavelength, and wherein the first spectral position is different from the second spectral position.

21. Apparatus for determining the analyte content of a sample, the apparatus comprising:

(a) a signal generator for generating a first input signal having a first wavelength, and a second input signal having a second wavelength, the two wavelengths differing by at least about 3 nanometers;

(b) a means for directing the first and second input signals to a sample containing an analyte to generate, respectively, a first output signal and a second output signal due to interactions between the input signals and the analyte, wherein the first output signal comprises: (i) a first resonant output signal whose peak wavelength is substantially independent of the wavelength of the first input signal, and (ii) a first non-resonant output signal whose peak wavelength is dependent on the wavelength of the first input signal, and wherein the second output signal comprises: (i) a second resonant output signal whose peak wavelength is substantially independent of the wavelength of the second input signal, and (ii) a second non-resonant output signal whose peak wavelength is dependent on the wavelength of the second input signal, and (c) a detector for detecting the first and second output signals; and (d) means for distinguishing the first resonant output signal from the second resonant output signal to obtain data about the analyte content of the sample.

22. Apparatus as claimed in claim 21 wherein the first resonant signal has a first spectrum comprising first and second component spectral curves, and wherein the second resonant signal has a second spectrum comprising a third and fourth component spectral curves, wherein the first and the third component spectral curves are related, and wherein the second and the fourth component spectral curves are related, and wherein the distinguishing means comprises means for distinguishing the first and the third related spectral curves from the second and the fourth related spectral curves.

23. Apparatus as claimed in claim 21 wherein the resonant output signals are signals responsive to molecular emission, including at least one of a fluorescence or phosphorescence signal.

24. Apparatus as claimed in claim 21 wherein the non-resonant output signals include at least one of a Rayleigh signal, Mie, Brillouin, and Raman scattering signal.

25. Apparatus for determining the analyte content of a sample, the apparatus comprising:

(a) a signal generator for generating a first input signal having a first wavelength, and a second input signal having a second wavelength, the two wavelengths differing by at least about 3 nanometers;

(b) a means for directing the first and second input signals to a sample containing an analyte to generate, respectively, a first output signal and a second output signal due to interactions between the input signals and the analyte, wherein the first output signal comprises: (i) a first resonant output signal whose peak wavelength is substantially independent of the wavelength of the first input signal, and (ii) a first non-resonant output signal whose peak wavelength is dependent on the wavelength of the first input signal, and wherein the second output signal comprises: (i) a second resonant output signal whose peak wavelength is substantially independent of the wavelength of the second input signal, and (ii) a second non-resonant output signal whose peak wavelength is dependent on the wavelength of the second input signal, and (c) a detector for detecting the first and second output signals; and (d) means for distinguishing the first non-resonant output signal from the second non-resonant output signal to obtain data about the analyte content of the sample.

26. Apparatus as claimed in claim 25 wherein the first non-resonant output signal has a first spectrum and the second non-resonant output signal has a second spectrum, wherein the first and the second spectra are unrelated, and wherein the distinguishing means comprises means for distinguishing between the unrelated spectra.

27. A method for determining the analyte content of a sample, the method comprising the steps of:

(a) generating a first input signal having a first wavelength, and a second input signal having a second wavelength, the two wavelengths differing by at least about 3 nanometers;

(b) directing the first and second input signals to a sample containing an analyte to generate, respectively, a first output signal and a second output signal due to interactions between the input signals and the analyte, wherein the first output signal comprises: (i) a first resonant output signal whose peak wavelength is substantially independent of the wavelength of the first input signal and (ii) a first non-resonant output signal whose peak wavelength is dependent upon the wavelength of the first input signal, and wherein the second output signal comprises: (i) a second resonant output signal whose peak wavelength is substantially independent of the wavelength of the second input signal, and (ii) a second non-resonant output signal whose peak wavelength is dependent on the wavelength of the second input signal;

(c) detecting the first and the second output signals; and (d) distinguishing the resonant output signals from the non-resonant output signals to obtain data about the analyte content of the sample.

28. The method of claim 27 wherein the step of generating the first and the second input signals comprises: (i) generating the signals from two separate sources, each one for generating a source signal, and (ii) modulating the source signals for selectively directing the source signals to the sample as input signals.

29. The method of claim 28 wherein the sources comprise laser diodes operating at different wavelengths.

30. The method of claim 28 wherein the step of modulating the source signals comprises modulating the signals using a wavelength modulating device, and wherein the step of directing the source signals comprises guiding the signals via a fiberoptic waveguide having a common waveguide and two limbs, each limb being directed to one of the sources, and the common waveguide being directed to the wavelength modulating device.

31. The method of claim 30 wherein the step of modulating the generated signals comprises modulating the signals by a liquid crystal filter.

32. The method of claim 27 comprising the additional step of filtering the output signals immediately before the step of detecting the output signals.

33. The method of claim 27 wherein the resonant output signals are signals responsive to molecular emission, including at least one of a fluorescence or phosphorescence signal.

34. The method of claim 27 wherein the non-resonant signals include at least one of a Rayleigh signal, Mie, Brillouin, and Raman scattering signal.

35. The method of claim 27 wherein the step of generating the input signals comprises generating the input signals such that the first and second resonant output signals have substantially the same spectra.

36. The method of claim 27 wherein the step of distinguishing the output signals comprises expressing the first and the second resonant output signals as a single eigenvector, wherein the first and the second non-resonant output signals are not capable of being expressed as a single eigenvector.

37. The method of claim 27 wherein the step of distinguishing the output signals comprises selecting a predetermined number of eigenvectors for expressing the first and the second resonant output signals.

38. The method of claim 27 wherein the step of distinguishing the output signals comprises applying principal components regression analysis to the first output and second output signals, whereby the resonant output signals are distinguished from the non-resonant output signals.

39. The method of claim 27 wherein the step of distinguishing the output signals comprises applying a multivariate quantitative analysis to the first and the second output signals, whereby the first and the second resonant output signals are distinguished from the first and the second non-resonant output signals.

40. The method of claim 39 wherein the step of generating the input signals comprises generating the signals such that the first and the second wavelengths are separated by about 3 nanometers to about 40 nanometers.

41. The method of claim 38 wherein the first and the second resonant output signals have a first and a second spectrum respectively, and wherein the first and the second non-resonant output signals have a third and a fourth spectrum respectively, and wherein the step of generating the input signals comprises selecting the first and the second wavelengths such that the first and the second spectra are substantially the same, and such that the third and the fourth spectra are different, and wherein the step of applying principal components regression analysis comprises (i) retaining the first and the second resonant output signals having the same spectra and (ii) rejecting the first and the second non-resonant output signals having different spectra.

42. The method of claim 27 wherein the step of generating the input signals comprises generating the first and the second input signals in sequence, and wherein the first and the second non-resonant output signals comprise first and second Raman signals respectively, the first and the second Raman signals having a first and a second Raman spectrum respectively, and wherein the first Raman spectrum is at a first spectral position dependent on the first wavelength, and the second Raman spectrum is at a second spectral position dependent on the second wavelength, and wherein the first spectral position is different from the second spectral position.

43. The method of claim 27 wherein the step of generating the input signals comprises generating the first and the second input signals in sequence, and wherein the first and the second non-resonant output signals comprise first and second Rayleigh scattering signals respectively, the first and the second Rayleigh signals having a first and a second Rayleigh spectrum respectively, and wherein the first Rayleigh spectrum is at a first spectral position dependent on the first wavelength, and the second Rayleigh spectrum is at a second spectral position dependent on the second wavelength, and wherein the first spectral position is different from the second spectral position.

44. A method for determining the analyte content of a sample, the method comprising the steps of:

(a) generating a first input signal having a first wavelength, and a second input signal having a second wavelength, the two wavelengths differing by at least about 3 nanometers;

(b) directing the first and second input signals to a sample containing an analyte to generate, respectively, a first output signal and a second output signal due to interactions between the input signals and the analyte, wherein the first output signal comprises: (i) a first resonant output signal whose peak wavelength is substantially independent of the wavelength of the first input signal, and (ii) a first non-resonant output signal whose peak wavelength is dependent on the wavelength of the first input signal, and wherein the second output signal comprises: (i) a second resonant output signal whose peak wavelength is substantially independent of the wavelength of the second input signal, and (ii) a second non-resonant output signal whose peak wavelength is dependent on the wavelength of the second input signal, and (c) detecting the first and second output signals; and (d) distinguishing the first resonant output signal from the second resonant output signal to obtain data about the analyte content of the sample.

45. The method of claim 44 wherein the first resonant output signal has a first spectrum comprising first and second component spectral curves, and wherein the second resonant output signal has a second spectrum comprising third and fourth component spectral curves, wherein the first and the third component spectral curves are related, and wherein the second and the fourth component spectral curves are related, and wherein the step of distinguishing the output signals comprises distinguishing the first and the third related spectral curves from the second and the fourth related spectral curves.

46. The method of claim 44 wherein the resonant output signals are signals responsive to molecular emission, including at least one of a fluorescence or phosphorescence signal.

47. The method of claim 44 wherein the non-resonant signals include at least one of a Rayleigh signal, Mie, Brillouin, and Raman scattering signal.

48. A method for determining the analyte content of a sample, the method comprising the steps of:

(a) generating a first input signal having a first wavelength, and a second input signal having a second wavelength, the two wavelengths differing by at least about 3 nanometers;

(b) directing the first and second input signals to a sample containing an analyte to generate, respectively, a first output signal and a second output signal due to interactions between the input signals and the analyte, wherein the first output signal comprises: (i) a first resonant output signal whose peak wavelength is substantially independent of the wavelength of the first input signal, and (ii) a first non-resonant output signal whose peak wavelength is dependent on the wavelength of the first input signal, and wherein the second output signal comprises: (i) a second resonant output signal whose peak wavelength is substantially independent of the wavelength of the second input signal, and (ii) a second non-resonant output signal whose peak wavelength is dependent on the wavelength of the second input signal, and (c) detecting the first and second output signals; and (d) distinguishing the first non-resonant output signal from the second non-resonant output signal to obtain data about the analyte content of the sample.

49. The method of claim 48 wherein the first non-resonant signal has a first spectrum and the second non-resonant signal has a second spectrum, wherein the first and the second spectra are unrelated, and wherein the step of distinguishing the output signals comprises distinguishing between the unrelated spectra.

* * * * *